(12) United States Patent
Garcia et al.

(10) Patent No.: US 9,598,703 B2
(45) Date of Patent: Mar. 21, 2017

(54) CAPSID-FREE AAV VECTORS, COMPOSITIONS, AND METHODS FOR VECTOR PRODUCTION AND GENE DELIVERY

(75) Inventors: Luis Garcia, Noisy-le-Roi (FR); Cyriaque Beley, Fontenay le Fleury (FR); Thomas Voit, London (GB); Robert Michael Kotin, Bethesda, MD (US); Lina Li, Potomac, MD (US)

(73) Assignees: ASSOCIATION INSTITUT DE MYOLOGIE; UNIVERSITÉ PIERRE ET MARIE CURIE (PARIS 6); CENTRE NATIONAL DE LA RECHERCHE SCIENTIFIQUE; INSTITUT NATIONAL DE LA SANTÉ DE LAD RECHERCHE MÉDICALE (FR); THE UNITED STATES OF AMERICA, AS REPRESENTED BY THE DEPARTMENT OF HEALTH AND HUMAN SERVICES, NATIONAL INSTITUTES OF HEALTH, Washington, DC (US)

( * ) Notice: Subject to any disclaimer, the term of this patent is extended or adjusted under 35 U.S.C. 154(b) by 213 days.

(21) Appl. No.: 14/004,379

(22) PCT Filed: Mar. 12, 2012

(86) PCT No.: PCT/EP2012/054303
§ 371 (c)(1),
(2), (4) Date: Dec. 20, 2013

(87) PCT Pub. No.: WO2012/123430
PCT Pub. Date: Sep. 20, 2012

(65) Prior Publication Data
US 2014/0107186 A1    Apr. 17, 2014

Related U.S. Application Data

(60) Provisional application No. 61/452,071, filed on Mar. 11, 2011.

(30) Foreign Application Priority Data

Mar. 12, 2011   (EP) ...................................... 11157986

(51) Int. Cl.
*C12N 15/11* (2006.01)
*A61K 35/12* (2015.01)
(Continued)

(52) U.S. Cl.
CPC .... *C12N 15/86* (2013.01); *C12N 2750/14143* (2013.01); *C12N 2750/14171* (2013.01); *C12N 2800/24* (2013.01)

(58) Field of Classification Search
USPC ................................................ 536/23.1, 24.5
See application file for complete search history.

(56) References Cited

U.S. PATENT DOCUMENTS

2006/0088936 A1   4/2006   Warrington et al.

FOREIGN PATENT DOCUMENTS

WO        9618727 A1     6/1996

OTHER PUBLICATIONS

Himeda et al. (Methods Mol. Biol., 2011 vol. 709:pp. c1-19).*
(Continued)

*Primary Examiner* — Terra C Gibbs
(74) *Attorney, Agent, or Firm* — Leason Ellis LLP

(57) ABSTRACT

An isolated linear nucleic acid molecule comprising in this order: a first adeno-associated virus (AAV) inverted terminal repeat (ITR), a nucleotide sequence of interest and a second AAV ITR, wherein said nucleic acid molecule is devoid of AAV capsid protein coding sequences. The said nucleic acid
(Continued)

molecule can be applied to a host at repetition without eliciting an immune response. Methods for producing and purifying this nucleic acid molecule, and use of the same for therapeutic purposes are also provided.

17 Claims, 10 Drawing Sheets

(51) Int. Cl.
A61N 1/30 (2006.01)
C12N 15/86 (2006.01)

(56) References Cited

OTHER PUBLICATIONS

Scanlon KJ (Current Pharmaceutical Biotechnology, 2004 vol. 5:415-420).*
McCarty. "Self-complementary AAV Vectors; Advances and Applications." The American Society of Gene Therapy. vol. 16. No. 10. 2008. pp. 1648-1656.
Nahreini et al. "Cloning and Integration of DNA Fragments in Human Cells via the Inverted Terminal Repeats of the Adeno-Associated Virus 2 Genome." Gene. vol. 119. 1992. pp. 265-272.
Ward et al. "Minimum Origin Requirement for Linear Duplex AAV DNA Replication in Vitro." Virology. vol. 209. 1995. pp. 692-695.
International Search Report for International Application No. PCT/EP2012/054303 mailed May 3, 2012. 3 pages.

* cited by examiner

A)

B)

A)

B) AAVo injected limb
(2 weeks after infusion)
*Macroscopic view*
White light     FITC filter Control leg (non-injected)
*Macroscopic view*
White light     FITC filter

C)

CAPSID-FREE AAV VECTORS, COMPOSITIONS, AND METHODS FOR VECTOR PRODUCTION AND GENE DELIVERY

This application is a National Stage Application of PCT/EP2012/054303, filed Mar. 12, 2012, which claims benefit of Ser. No. 61/452,071, filed Mar. 11, 2011 in the United States and Serial No. 11157986.8, filed Mar. 12, 2011 in the European Patent Office. Each of the above-named applications is incorporated herein by reference in its entirety. To the extent appropriate, a claim of priority is made to each of the above-named applications.

TECHNICAL FIELD

The present invention relates to methods of delivering exogenous, particularly heterologous, DNA sequences to a target, particularly a target cell, tissue, organ or organism. In particular, the invention relates to novel naked adeno-associated virus (AAV) vectors devoid of viral capsid proteins (hereinafter "AAV0") for the delivery to targets of heterologous DNA sequences. Recombinant AAV0 vectors of the invention may be used for in vitro, ex vivo, or in vivo delivery of an exogenous DNA sequence to a target. The invention also provides for methods of producing and purifying AAV0 vectors.

BACKGROUND OF THE INVENTION

Gene therapy aims to correct defective genes that underlie the development of diseases. A common approach to addressing this issue involves the delivery of a normal gene to the nucleus. This gene may then be inserted into the genome of the targeted cell or may remain episomal. Delivery of a corrective gene to a subject's target cells can be carried out via numerous methods, including the use of viral vectors. Among the many viral vectors available (e.g., retrovirus, lentivirus, adenovirus, and the like), adeno-associated virus (AAV) is gaining popularity as a versatile vector in gene therapy.

Adeno-associated virus (AAV) is a member of the parvoviridae family. The AAV genome is composed of a linear single-stranded DNA molecule which contains approximately 4.7 kilobases (kb) and consists of two major open reading frames encoding the non-structural Rep (replication) and structural Cap (capsid) proteins. Flanking the AAV coding regions are two cis-acting nucleotide inverted terminal repeat (ITR) sequences, approximately 145 nucleotides in length, with interrupted palindromic sequences that can fold into hairpin structures that function as primers during initiation of DNA replication. In addition to their role in DNA replication, the ITR sequences have been shown to be necessary for viral integration, rescue from the host genome, and encapsidation of viral nucleic acid into mature virions (Muzyczka, (1992) Curr. Top. Micro. Immunol. 158:97-129).

Vectors derived from AAV are particularly attractive for delivering genetic material because (i) they are able to infect (transduce) a wide variety of non-dividing and dividing cell types including muscle fibers and neurons; (ii) they are devoid of the virus structural genes, thereby eliminating the natural host cell responses to virus infection, e.g., interferon-mediated responses; (iii) wild-type viruses have never been associated with any pathology in humans; (iv) in contrast to wild type AAVs, which are capable of integrating into the host cell genome, replication-deficient AAV vectors generally persist as episomes, thus limiting the risk of insertional mutagenesis or activation of oncogenes; and (v) in contrast to other vector systems, AAV vectors do not trigger a significant immune response (see ii), thus granting long-term expression of the therapeutic transgenes (provided their gene products are not rejected). AAV vectors can also be produced at high titer and intra-arterial, intra-venous, or intra-peritoneal injections allow gene transfer to significant muscle regions through a single injection, at least in rodents (Goyenvalle et al., 2004; Fougerousse et al., 2007; Koppanati et al., 2010; Wang et al., 2009). AAV vectors also have multiple advantages over plasmid DNA with respect to delivering genetic material. For instance, expression of heterologous genes from plasmids is short-term, plasmids are usually of greater size, and plasmids need to be physically manipulated in order to be delivered into cells (e.g., microinjection, transfection, electroporation). Furthermore, plasmid transfer of genes such as dystrophin elicits an immune response in the host and is associated with low efficiency (Romero et al., 2004).

However, the use of conventional AAV as a gene delivery vector is also associated with numerous drawbacks. First, a significant proportion of potential recipients of such therapy are already seropositive to a given type of AAV vector (Boutin et al., 2010). Second, in some individuals AAV vectors may elicit a mild host immune response likely mediated by the viral capsid or processing impurities. In this context, use of immunosuppressants to control the immune response is only a temporary measure, as once a subject is taken off these immunosuppressants, the immune response returns (Lorain et al., 2008). Perhaps the main drawback associated with AAV is its limited viral packaging capacity of about 4.5 kb of heterologous DNA (Dong et al., 1996; Athanasopoulos et al., 2004; Lai et al., 2010).

Different approaches using dual-vector strategies have been attempted to expand AAV vector packaging capacity, such as trans-splicing (ts) and overlapping (ov) AAV vector systems designed to deliver large therapeutic genes to target cells. For instance, Lostal et al. bypassed the size limitation with respect to dysferlin cDNA, which cannot be directly incorporated into an AAV vector for gene transfer into muscle, by splitting the dysferlin cDNA at the exon 28/29 junction and cloning it into two independent AAV vectors carrying appropriate splice sequences (Lostal et al., 2010). Yet, even these approaches suffer from inherent inefficiency. Thus, the small packaging capacity remains a major limitation in AAV gene therapy. Removal of the capsid has not been considered a way by which the packaging capacity could be overcome because the capsid is considered essential to permit vector entry into the cell.

Another notable drawback is that AAV-mediated gene expression is relatively slow, given that single-stranded AAV DNA must be converted to double-stranded DNA prior to heterologous gene expression. While attempts have been made to circumvent this issue by constructing double-stranded DNA vectors, this strategy further limits the size of the transgene expression cassette that can be integrated into the AAV vector (McCarty, 2008; Varenika et al., 2009; Foust et al., 2009). Furthermore, effective AAV-mediated gene therapy in a growing organ can lose its effect due to episomal DNA dilution in dividing cells (Cunningham et al., 2009).

The present invention addresses some or all of the aforementioned drawbacks associated with AAV vectors by providing recombinant AAV0 ("rAAV0") vectors for in vitro, ex vivo, or in vivo delivery of exogenous DNA sequences to a cell, tissue, organ, or subject.

SUMMARY OF THE INVENTION

The present invention is based on the finding that exogenous DNA sequences can be incorporated into AAV genomes (or vectors) devoid of capsids (i.e., AAV0) and delivered into target cells, tissues, organs, or subjects for efficient expression of a protein or ribonucleotide (RNA) or desoxyribonucleotide (DNA) of interest without mediation of the uptake process by a viral capsid. Prior to the present invention, the capsid was considered necessary for the efficient uptake of the viral vector into the cell and there would have been a reluctance to dispense with it. In fact, methods for purifying AAV vectors were largely based on antibodies against the capsid which would leave nonencapsidated DNA behind or on use of DNAase that would have degraded any nonencapsidated DNA.

Structural features distinguishing the rAAV0 vectors of the present invention from plasmid-based expression vectors include the lack of original (i.e. not inserted) bacterial DNA in rAAV0 vectors, rAAV0 vectors lack a prokaryotic origin of replication, rAAV0 vectors are self-containing, i.e., they do not require any sequences other than the two ITRs, including the Rep binding and terminal resolution sites (RBS and TRS), and an exogenous sequence between the ITRs, the presence of ITR sequences that form hairpins, the fact that rAAV0 vectors are of eukaryotic origin (i.e., they are produced in eukaryotic cells) and the absence of bacterial-type DNA methylation or indeed any other methylation considered abnormal by a mammalian host. In general, it is preferred for the present vectors not to contain any prokaryotic DNA but it is contemplated that some prokaryotic DNA may be inserted as an exogenous sequence. Another important feature distinguishing rAAV0 vectors from plasmid expression vectors is that rAAV0 vectors consist in both single-stand or double-strand linear DNA, while plasmids are always double-stranded DNA.

Some of the advantages of rAAV0 vectors of the present invention over plasmid-based expression vectors include, but are not limited to: 1) plasmids contain bacterial DNA sequences and are subjected to prokaryotic-specific methylation, i.e. purine base methylation, whereas rAAV0 vector sequences are of eukaryotic origin; 2) while plasmids require the presence of a resistance gene during the production process, rAAV0 vectors do not; 3) while a circular plasmid is not delivered to the nucleus upon introduction into a cell and requires overloading to bypass degradation by cellular nucleases, rAAV0 vectors contain viral cis-elements, i.e., ITRs, that confer resistance to nucleases and can be designed to be targeted and delivered to the nucleus. It is hypothesized that the minimal defining elements indispensable for ITR function are a Rep-binding site (RBS; 5'-GCGCGCTCGCTCGCTC-3' for AAV2) and a terminal resolution site (TRS; 5'-AGTTGG-3' for AAV2) plus a variable palindromic sequence allowing for hairpin formation.

Advantages of rAAV0 vectors over conventional AAV vectors include, but are not limited to: 1) conventional AAV vectors have capsids that elicit a host immune response, whereas such a response is not triggered by capsid-less rAAV0 vectors; 2) conventional AAV vectors have limited cargo capacity (approximately 4.5 kb), whereas rAAV0 vectors are not subject to this limit, i.e., they can incorporate sequences from very short ones to more than 10% longer than the cargo capacity of the wild-type AAV genome, i.e. about 5 kbase up to 8, 10 or even 15 kb; 3) preparations of conventional AAV vectors are inhomogeneous (i.e., contain mixtures of complete AAV vectors and empty capsids), whereas rAAV0 vectors are substantially homogeneous in nature; and 4) the composition of conventional AAV vectors is heterogeneous even after purification, whereas rAAV0 vectors can be characterized fully using standard DNA analytical techniques allowing one to obtain a homogenous and completely characterized end product. Furthermore, given the lack of immunogenicity of rAAV0 vectors, mixtures of different rAAV0 vectors can be co-administered to a cell, organ, or subject, either through identical or different routes.

Generally, the invention provides rAAV0 vectors and their use for expressing proteins or RNA or DNA in, for example, cells, organs, tissues, and subjects. Such expression is not limited to one protein or RNA molecule, but can involve the expression of multiple proteins and/or RNAs via multiple distinct rAAV0 vectors delivered into the host. Such transduction can be transient or permanent. For example, rAAV0 vectors that encode a product intended to elicit a permanent modification or correction of the host genome (e.g., via a meganuclease or zinc finger nuclease) can be transiently transduced into the host. In other aspects, rAAV0 vectors can deliver coding or non-coding DNA that can influence gene editing, such as exon skipping. rAAV0 vectors of the invention can also be employed for vaccination by delivering a rAAV0 vector encoding a protein or a protein/DNA mixture by intramuscular injection followed by a second injection, preferably intramuscular, both injections conveying the expression of the same antigen (protein) which is not recognized by the immune repertoire of the host (self). rAAV0 vectors of the invention have utility for transgene delivery into embryonic stem cells (ESCs) or ovary cells for the generation of genetic knock-out or knock-in animal models. rAAV0 vectors of the invention can also be used to induce immune tolerance to a gene product by application in the neonatal period in order to pave the way for subsequent immune-tolerance for a substitutive therapy such as an enzyme therapy (Sun, B, et al *Am. J. Hum. Genet.* 2007; 81:1042-1049). For example, Balb/c mice are sensitive and mount both cellular and humoral immune responses to GFP. By injecting them with a small amount of rAAV0 carrying GFP gene at birth, tolerance can be induced such that subsequent injections of larger amounts of rAAV0 or other GFP carrying vector will not elicit significant immune responses.

In one aspect, the invention provides an isolated linear nucleic acid molecule comprising in this order: a first adeno-associated virus (AAV) inverted terminal repeat (ITR), a nucleotide sequence of interest (for example an expression cassette of an exogenous DNA) and a second AAV ITR, wherein said nucleic acid molecule is devoid of AAV capsid protein coding sequences. In a further embodiment, the nucleic acid molecule of the invention is devoid of viral capsid protein coding sequences (i.e. it is devoid of AAV capsid genes but also of capsid genes of other viruses). In addition, in a particular embodiment, the nucleic acid molecule is also devoid of AAV Rep protein coding sequences. Accordingly, in a preferred embodiment, the nucleic acid molecule of the invention is devoid of functional AAV cap and AAV rep genes.

Accordingly, the invention provides for a minimal rAAV0 vector which has two AAV inverted terminal repeats (ITRs) and a nucleotide sequence of interest (for example an expression cassette), each of said ITRs having an interrupted (or noncontiguous) palindromic sequence, i.e., a sequence composed of three segments: a first segment and a last segment that are identical when read 5'→3' but hybridize when placed against each other, and a segment that is different that separates the identical segments. Such sequences, notably the ITRs, form hairpin structures. The nucleotide sequence of interest can in particular be an expression cassette comprising at least one promoter operatively linked to an exogenous DNA sequence, and flanked on each end by one ITR. The rAAV0 vector does not encode capsid proteins, and the rAAV0 vector is not encapsidated. The rAAV0 vector can be single-stranded, double-stranded, or duplex with one or both ends covalently linked via the ITR palindrome. In a preferred embodiment, the rAAV0 vector is single-stranded.

In one embodiment, the exogenous DNA sequence encodes a therapeutic protein, such as dystrophin; LARGE (Barresi et al., 2004); dysferlin; calpain 3; Dux 4; LAMA2; α-, β-, γ-, and δ-sarcoglycan; FKRP, fukutin, WASP, factor VIII, factor IX, SMN1, U7, modified U7 (U.S. Provisional Application 61/314,830 and WO2006/021724, both of which are hereby incorporated by reference in their entirety), U1, RdCVF (Léveillard et al., 2010), α-glucosidase, meganuclease or zinc-finger nuclease, and actin. In principle, however, any gene that encodes a protein or polypeptide that is either reduced or absent due to a mutation or which conveys a therapeutic benefit when overexpressed is considered to be within the scope of the invention. In other embodiments, the exogenous DNA sequences encode antisense oligonucleotides ("AONs") or RNAs (coding or non-coding) such as siRNAs, shRNAs, micro-RNAs, and their antisense counterparts (e.g., antagoMiR). In such cases, a mutated gene that causes a detrimental phenotype when expressed can be silenced in order to provide a therapeutic benefit. In yet another embodiment, the rAAV0 vector comprises a template nucleotide sequence used as a correcting DNA strand to be inserted after a double-strand break provided by a meganuclease- or zinc finger nuclease.

The rAAV0 vector of the invention may contain other introduced sequences from extraviral origin as desired. For example, a so-called suicide gene can be introduced to eliminate transduced cells. However, noninserted bacterial DNA is not present and preferably no bacterial DNA is present at all.

The rAAV0 vector of the invention can also be used in a method for the delivery of a nucleotide sequence of interest to a target cell. The method may in particular be a method for delivering a therapeutic gene of interest to a cell of a subject in need thereof. The invention allows for the in vivo expression of a polypeptide, protein, or oligonucleotide encoded by a therapeutic exogenous DNA sequence in cells in a subject such that therapeutic levels of the polypeptide, protein, or oligonucleotide are expressed. These results are seen with both in vivo and in vitro modes of rAAV0 vector delivery. The ability to deliver an exogenous DNA sequence to, for example, muscle cells by intramuscular administration in vivo provides a more efficient and convenient method of gene transfer. Thus in one embodiment, the invention relates to a method of delivering a selected gene into a cell, an organ, or tissue such as skeletal or cardiac muscle.

The invention, however, is not limited to the delivery and expression of a selected gene only in muscle cells, but is also applicable to other cell types in which expression of a therapeutic polypeptide, protein, or oligonucleotide is desired, for instance, neural cells. Thus, in another embodiment, the invention relates to rAAV0 vector-mediated delivery of a desired exogenous DNA sequence to neural cells by intracranial or intrathecal administration in vivo.

The invention should not be considered limiting with regard to the method of delivery. For example, delivery can be topical, intra-tissue (e.g., intramuscular, intracardiac, intrahepatic, intrarenal, intracerebral), conjunctival (e.g., extra-orbital, intraorbital, retroorbital, intraretinal, sub-retinal), mucosal (e.g., oral, rectal, nasal, pulmonary), intrathecal, intravesical, intracranial, systemic, intraperitoneal, subcutaneous, cutaneous, intravascular (e.g. intravenous, intraarterial), and intralymphatic. In other aspects, passive tissue transduction via high pressure intravascular infusion, e.g. intravenous or intraarterial infusion, and intracellular injection, such as intranuclear microinjection or intracytoplasmic injection, are also contemplated.

Furthermore, delivery is not limited to one species of rAAV0 vector. As such, in another aspect, multiple rAAV0 vectors comprising different exogenous DNA sequences can be delivered simultaneously or sequentially to the target cell, tissue, organ, or subject. Therefore, this strategy can allow for the expression of multiple genes. Delivery can also be performed multiple times and, importantly for gene therapy in the clinical setting, in subsequent increasing or decreasing doses, given the lack of an anti-capsid host immune response due to the absence of a viral capsid. It is anticipated that no anti-capsid response will occur as there is no capsid. This can be confirmed, if desired, by multiple injections along the lines of Example 5 (FIG. 7) and by measurement of antibody response or of specific T cell activation or proliferation. In addition, it is expected that even immunogenicity against a protein product of the transgene will be reduced if delivered by a single stranded rAAV0 because single strand AAV vectors are less capable of eliciting a strong innate immune response than double strand AAV vectors (Wu et al, 2011).

In still another aspect, the invention provides a method for making capsid-less rAAV0 vectors, notably a method with a sufficiently high yield to provide sufficient vector for in vivo experiments. The method includes providing cells comprising two AAV ITRs, a nucleotide sequence of interest (e.g. an expression cassette comprising usually at least one promoter operatively linked to an exogenous DNA except for the delivery of a pure DNA template) positioned between the ITRs. The nucleotide sequence of interest is flanked on each end by one ITR and does not encode AAV capsid proteins, and the cells do not express AAV capsid proteins. The cells either already contain Rep or are transduced with a vector to contain Rep and are then grown under conditions permitting replication and release of DNA comprising the ITRs and the expression cassette and constituting the rAAV0 vector. The rAAV0 vector can then be collected and purified from the cells or supernatant as free released rAAV0 vector or as exosomes or microparticles.

In yet another aspect, the invention provides for host cell lines that have stably integrated a rAAV0 genome into their own genome. In one embodiment, the host cell line is an invertebrate cell line, preferably insect Sf9 cells. In another embodiment, the host cell line is a mammalian cell line, preferably 293 cells. Although the use of plasmid transfection to introduce the AAV0 backbone for amplification in producing cells is not suitable for in vivo application into a mammal (e.g., a human), one could, as in the case of Sf9 cells, envisage the use of a second vector such as herpes virus to introduce Rep protein into cells, allowing for the excision and amplification of rAAV0. In yet another aspect, the Rep-encoding gene can be stably integrated into the host cell line (e.g., Sf9 cells). The means of introducing the Rep gene are multiple: e.g., transfection of plasmid, infection of a vector expressing Rep, stable cell lines expressing Rep. In yet another embodiment, the mammalian host cell is isolated from a subject afflicted with a disease. The autologous host cell is preferably isolated from tissue that is directly affected by the disease and fails to express normal levels of a gene product, expresses a mutated and either nonfunctional or poorly functional gene product, or aberrantly overexpresses a gene product leading to the disease.

In one aspect, the host cell is a stem cell. Thus, rAAV0 transduction can result in, for example, the transient transduction of a given stem cell population where the transferred episomal gene or non-coding RNA is diluted upon subsequent cell passages. Alternatively, rAAV0-mediated transfer of an engineered meganuclease can lead to lasting genetic modification in stem cells (Silva et al., 2011). In this case, while the meganuclease itself would be diluted upon subsequent cell divisions, the rAAV0-meganuclease-mediated genetic modification will be inherited in a Mendelian manner through subsequent cell divisions. This could rectify a major drawback of meganuclease use.

In yet another aspect, the invention provides for methods of purifying rAAV0 vectors from host cell lines that have stably integrated a rAAV0 genome into their own genome. Of note, the plasmid backbone is not suitable for rAAV0 production given its prokaryotic origin, which carries a significant risk of immunogenicity. rAAV0 production undergoes two steps: first, excision ("rescue") from the vector backbone via Rep proteins, and second, amplification of the excised vector genome by Rep proteins. Mere transfection of plasmids harboring AAV0 will result in mainly rescued rAAV0, with no or poor amplification. This highlights a further drawback of plasmids carrying AAV0 vectors: poor or no amplification. In one embodiment, rAAV0 vectors are purified as DNA molecules. In another embodiment, the rAAV0 vectors are purified as exosomes or microparticles.

The invention also provides for a method of treating a disease in a subject comprising introducing into a target cell in need thereof (in particular a muscle cell or tissue) of the subject a therapeutically effective amount of a rAAV0 vector, optionally with a pharmaceutically acceptable carrier. While the rAAV0 vector can be introduced in the presence of a carrier, such a carrier is not required. The rAAV0 vector implemented comprises a nucleotide sequence of interest useful for treating the disease. In particular, the rAAV0 vector may comprise a desired exogenous DNA sequence operably linked to control elements capable of directing transcription of the desired polypeptide, protein, or oligonucleotide encoded by the exogenous DNA sequence when introduced into the subject. The rAAV0 vector can be administered via any suitable route as provided above, and elsewhere herein. In a preferred embodiment, the disease is Duchenne muscular dystrophy (DMD) and the transgene is dystrophin or a rAAV0 encoding an optimized U7 harboring an appropriate antisense sequence allowing for the skipping of exon 23 in the mdx mouse model (see Goyenvalle et al., 2004). This rAAV0-U7 vector can be administered, for example, via intra-arterial injection of the femoral artery under parallel blockage of venous flow by a garrot proximal to the injection site. The resulting exon skipping and dystrophin restoration can be observed as soon as 4 weeks after administration to the transduced muscle tissue.

The invention further provides for a method of treating a genetic or acquired muscle disease or disorder (or simply adding a gene or suppressing one) in a subject by (1) establishing a myoblast culture from a muscle biopsy of a subject with the disease (Bigot et al., 2008; Benchaouir et al., 2007), (2) delivering a rAAV0 vector to myoblasts or to muscle tissue, the vector comprising the desired exogenous DNA sequence operably linked to control elements capable of directing transcription of the desired polypeptide, protein, or oligonucleotide encoded by the exogenous DNA sequence, (3) collecting exosomes or microparticles harboring the vector bearing the exogenous DNA sequence from the culture or collecting rAAV0 vectors in the form of DNA, and (4) delivering the collected rAAV0-filled exosomes or microparticles or rAAV0 vectors in the form of DNA into the subject. The exosomes or microparticles can have a particular tropism (e.g., muscle cell specific) and thereby have the capacity to transduce neighboring cells.

In another embodiment, stem cells isolated from a patient can be transduced ex vivo to correct the deficiency caused by a mutation of a gene product in a host, or alternatively, to correct a genetic defect using a rAAV0-encoded DNA-cutting enzyme such as a zinc finger nuclease (Connelly et al., 2010). In another embodiment, the DNA-cutting enzyme is a meganuclease (Silva et al., 2011). In yet another embodiment, the DNA-cutting enzyme is a TAL effector nuclease (Sun et al., 2012).

Stem cells, such as mesenchymal stem cells, hematopoietic stem cells, and iPS cells, are attractive targets for ex vivo modification with rAAV0 vectors for potential cellular and gene therapy of inherited and acquired disorders. Certain advantages that make these cell types ideal for therapy include their ability to differentiate into multiple lineages, their ability to proliferate and self-renew, migrate to injury sites, and the fact that they are hypoimmunogenic when transduced ex vivo, allowing transplantation back into the host upon correction of the underlying defect (Li et al., 2009; Benchaouir et al., 2007). Importantly, while many stem cell types are inefficiently transduced with viral vectors, including AAV (Id.), rAAV0 vectors can bypass this shortcoming due to their non-dependence on the viral capsid for cell entry, particularly when combined with microparticle- or exosome-mediated delivery. See, High-Efficiency Transduction of Fibroblasts and Mesenchymal Stem Cells by Tyrosine-Mutant AAV2 Vectors for Their Potential Use in Cellular Therapy. Li M, Jayandharan G R, Li B, Ling C, Ma W, Srivastava A, Zhong L., Hum Gene Ther. 2010; 21:1527-1543.

Other diseases that can be treated with rAAV0 include, but are not limited to, DMD, Spinal Muscular Atrophy, Pompe disease, Parkinson's disease, Huntington disease, Alzheimer disease, ALS, epilepsy, stroke, cystic fibrosis, and solid tumors. In a preferred embodiment, the disease is DMD. A particularly interesting application will be the use of AAV0 in cancer therapy because of the ability to repeat the treatment until a tumor is reduced or eliminated, since no immune response is anticipated with the rAAV0 vector of the invention.

These and other embodiments, features and advantages of the disclosure will become apparent from the detailed description and the appended claims set forth herein below.

BRIEF DESCRIPTION OF THE DRAWINGS

FIG. 2a shows a 5 L bioreactor (B. Braun Medical Inc.), which can be used to amplify AAV0 in Sf9 cells, and an Akta Purifier 100 (B. Braun Medical Inc.), which can be used for downstream AAV0 purification processes. FIG. 2b is a schematic detailing the AAV0 amplification process and downstream purification process using the Sf9 cell system.

Outside the region sandwiched between and including the two ITRs is a blasticidin S-resistance gene, which is operably linked to the *Orgyia pseudotsugata* immediate early-1 (Op IE-1) promoter.

Figure 3A:
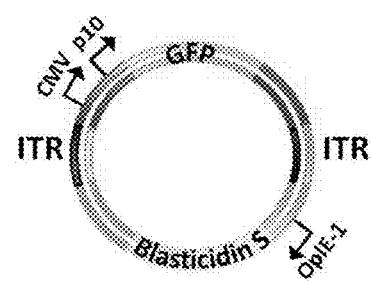
FIG. 3a is a schematic of the AAV0-GFP plasmid, which is based on the pFBGR plasmid and is used to make AAV0 in host cells. An ITR from AAV2 flanks both ends of the GFP expression cassette. The GFP expression cassette comprises, in the direction of transcription, a cytomegalovirus (CMV) promoter, a p10 promoter, and a DNA sequence encoding GFP, and a transcriptional termination sequence.
Figure 3B:
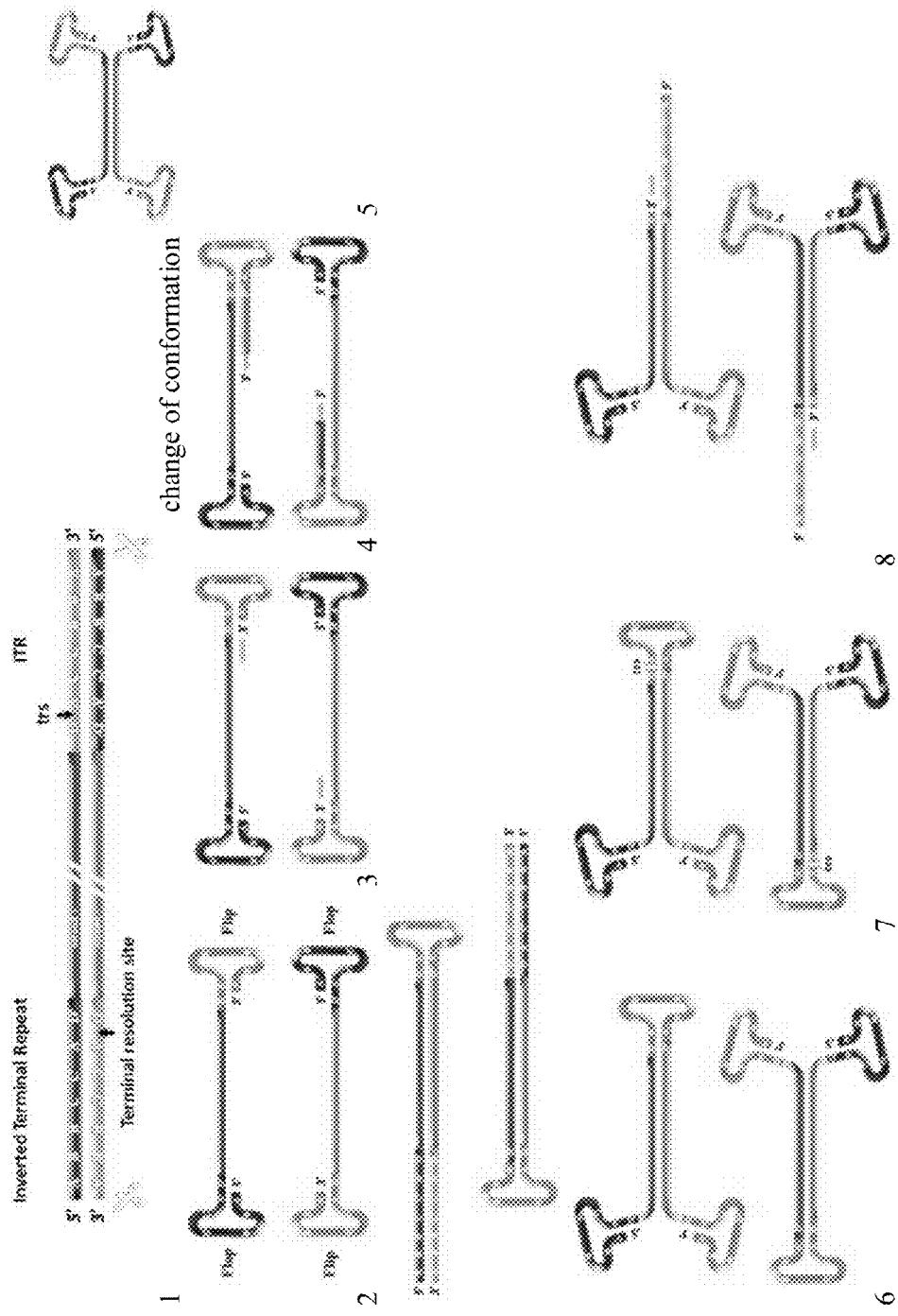
Figure 3B:
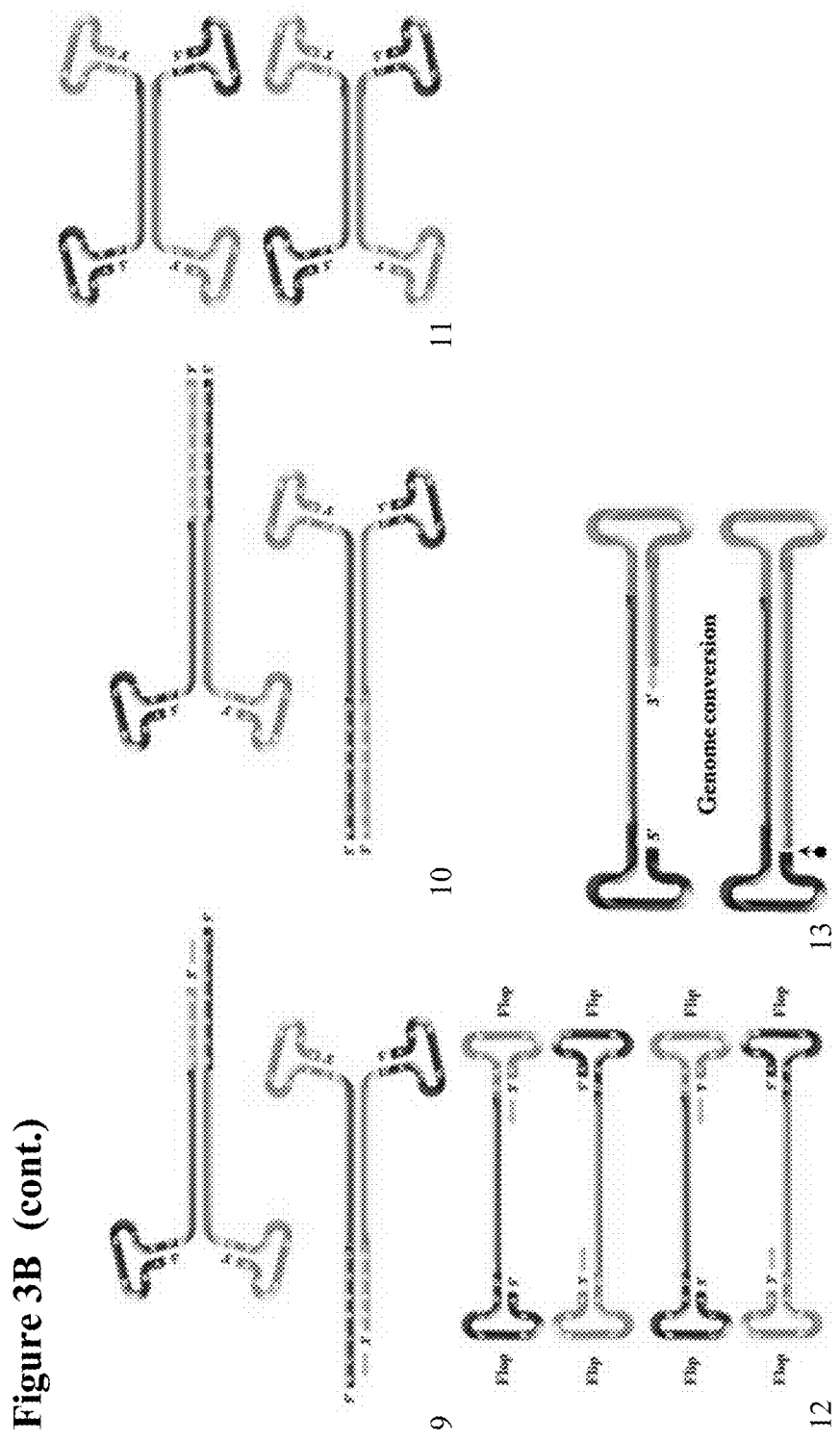

FIG. 3b is a schematic representation of the general process of AAV genome amplification. In the presence of Rep, the AAV genome is removed from the host genome and is amplified (Berns et al., 2007; Nash et al., 2007).

Figure 4:
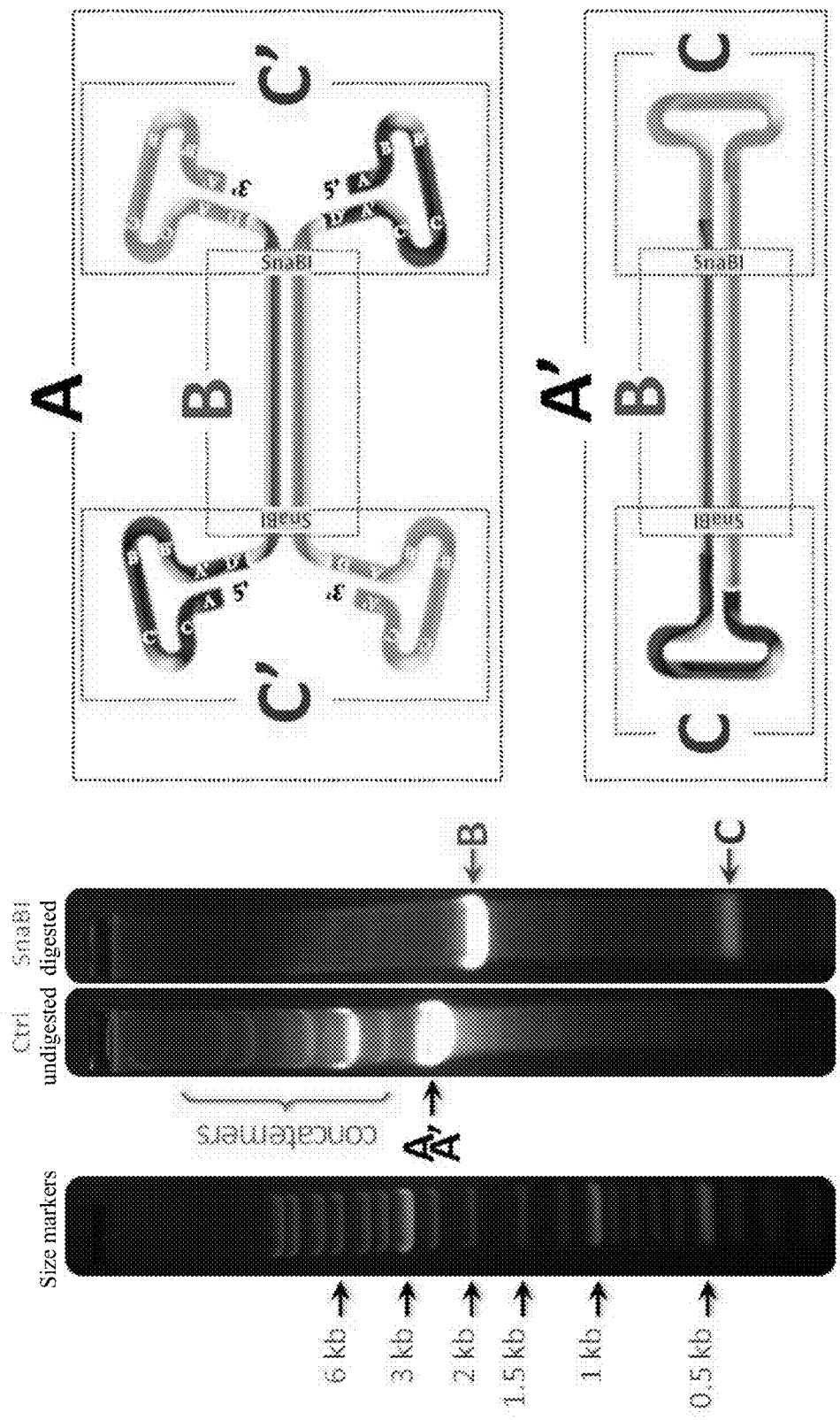

FIG. 4 is an agarose gel of undigested rAAV0 vector or rAAV0 vector digested with SnaBI enzyme. The bands on the agarose gel reflect the various conformations of rAAV0 (depicted in the schematic on the right) after DNA recovery at the end of the production process. The bands in the first lane of the agarose gel are DNA size markers. The second lane, labeled "Ctrl", is DNA from undigested rAAV0. Bands corresponding to rAAV0 concatemers are indicated. The letters "A" and "A'" reflect DNA products shown in the schematic on the right. The vast majority of rAAV0 is in monomeric form (double-stranded or converted ~2.5 kb). The bands in the third lane labeled "SnaBI", are DNA from rAAV0 digested with SnaBI enzyme. The letters "B" and "C" reflect DNA products shown in the schematic on the right. SnaBI digestion releases a 380 bp fragment containing the ITR (band "C").

Figure 5:
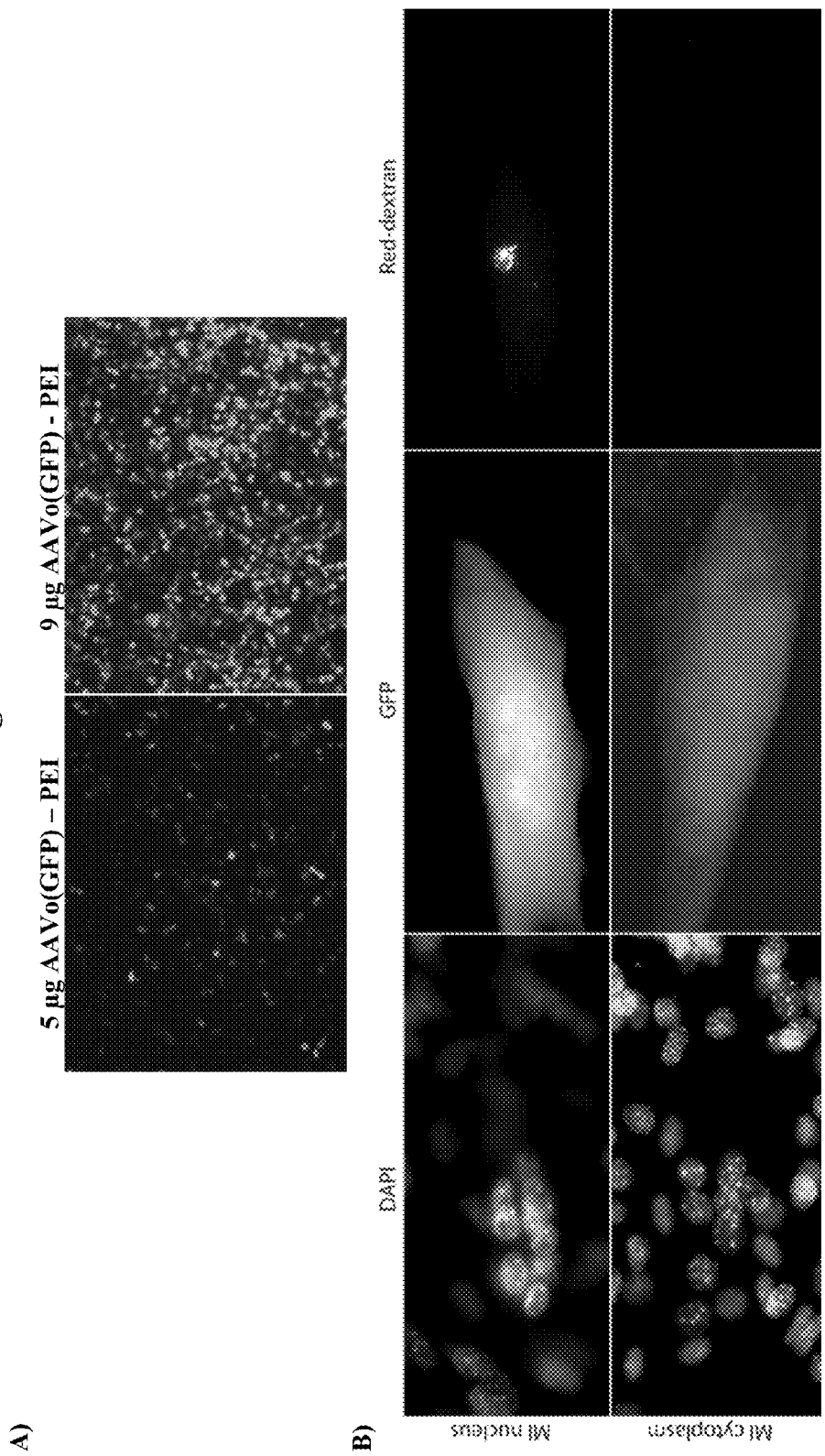

FIG. 5a is a fluorescence micrograph of 293 cells transfected with rAAV0-GFP vector using polyethylenimine (PEI) as a transfection reagent. $1\times10^6$ cells were transfected with 5 µg (left panel) and 9 µg (right panel) of rAAV0-GFP for 48 hours. FIG. 5b is a fluorescence micrograph of C2C12 myoblasts microinjected with a solution (0.02 mg/ml) of AAV0-GFP vector either into nuclei (Upper panel) or into cytoplasm (Lower panel) by using a Xenoworks microinjection system (Sutter Instruments). Tetramethylrhodamine 70,000 MW lysine-fixable dextran (Sigma) was also co-microinjected as an area marker of microinjection. Two days after microinjections, myotubes were fixed using paraformaldehyde 3.7% (Sigma) and permeabilized with 0.5% triton before further fluorescent stainings. Left panels show nuclei stained by DAPI (Sigma). Middle panels show GFP fluorescence. Right panels show dextran staining allowing for the confirmation of the microinjection site (nucleus versus cytoplasm). Fluorescent images were acquired using a Nikon Ti microscope equipped with a CoolSNAP HQ2 camera (Roper Scientific), using a 40×1.0 NA PL APO oil objective, driven by Metamorph (Molecular Devices).

Figure 6:
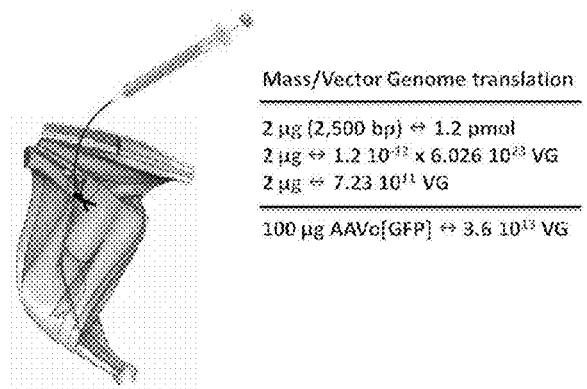
Figure 6:
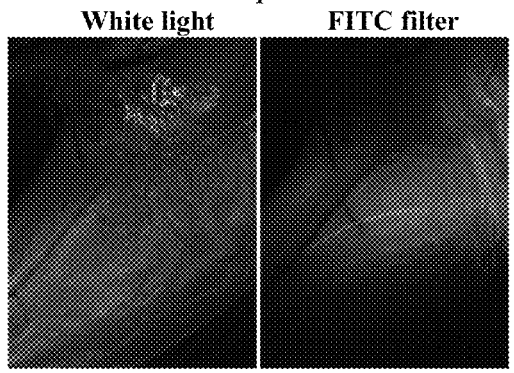
Figure 6:
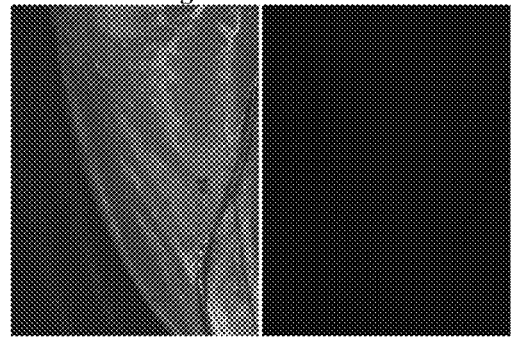
Figure 6:
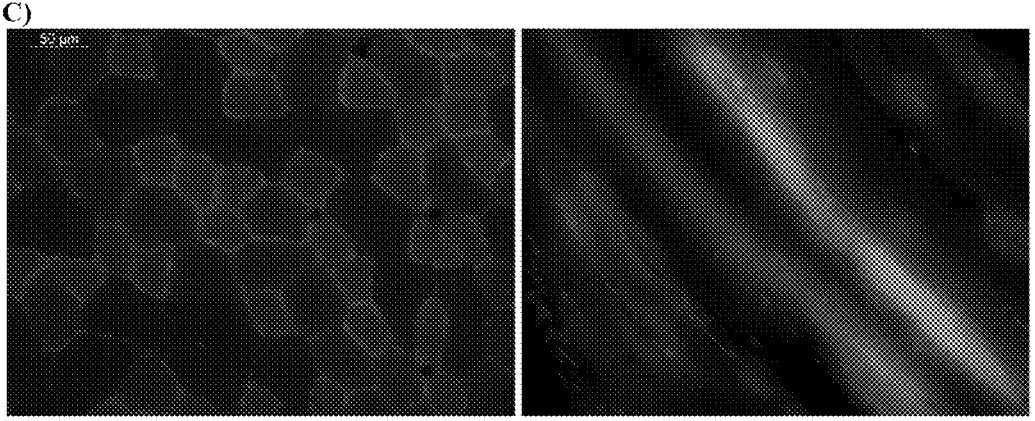

FIG. 6a is a scheme of a mouse leg being injected intra-arterially with AAV0-GFP (100 µg of AAV0-GFP in 1 ml of PBS). FIG. 6b is a fluorescence micrograph of a mouse leg that has been injected (two left panels) and one that has not been injected (two right panels); it shows that without intra-arterial injection of AAV0-GFP, no GFP signal is visible (right 35 panels). Left panels show that intra-arterial injection of AAV0-GFP results in efficient expression of GFP in the leg after two weeks. FIG. 6c shows GFP expression in cryosections of muscle tissue after intra-arterial injection of the leg (transversal (left panel) and longitudinal (right panel) 10 µm muscle sections). Nuclei were counterstained with DAPI black circles.

Figure 7:
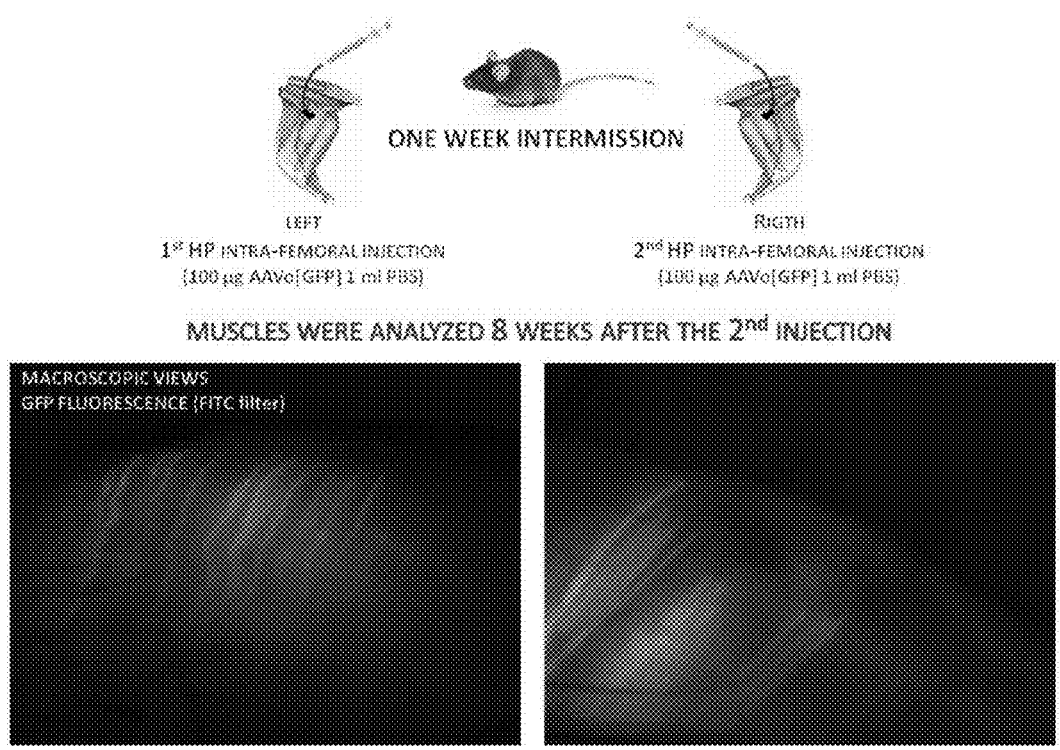

FIG. 7 is a fluorescence micrograph of mouse leg after two intra-arterial injections of AAV0-GFP in 1 week intervals. As shown in the scheme in the upper panel, the first injection was performed in the left leg (100 µg of AAV0-GFP in 1 ml of PBS), and the second in the right leg (100 µg of AAV0-GFP in 1 ml of PBS). Mice were allowed to recover for 8 weeks after the second injection prior to analysis. Fluorescence micrographs in the lower panel show that both legs were transduced with equal efficiency, suggesting that the first injection did not have a negative effect on the second injection.

Figure 8:
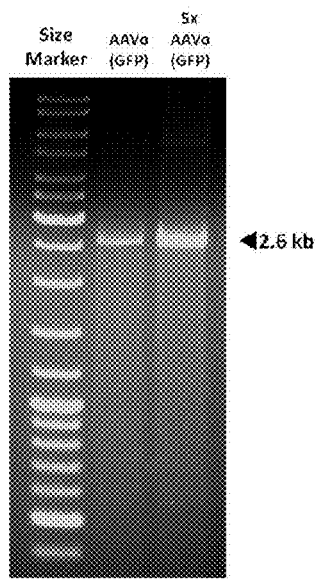

FIG. 8 is an agarose gel (1%) of undigested rAAV0 vector (encoding GFP under the CMV promoter) (300 ng middle lane, and 1.5 µg right lane). The bands on the agarose gel (2.6 kbase) reflect the linear monomeric single-stranded structure of rAAV0 after DNA recovery at the end of the production process. The bands in the left lane of the agarose gel are DNA size markers.

Figure 9:
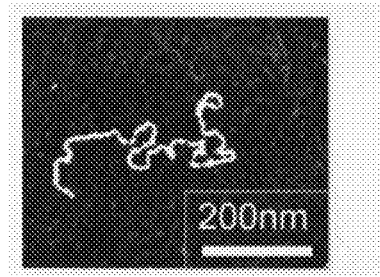

FIG. 9 is an electron microscopy micrograph of AAVo in the presence of SSB (single strand binding protein). AAVo appears as a linear structure, which is single stranded as revealed by SSB embodiment.

Figure 10:
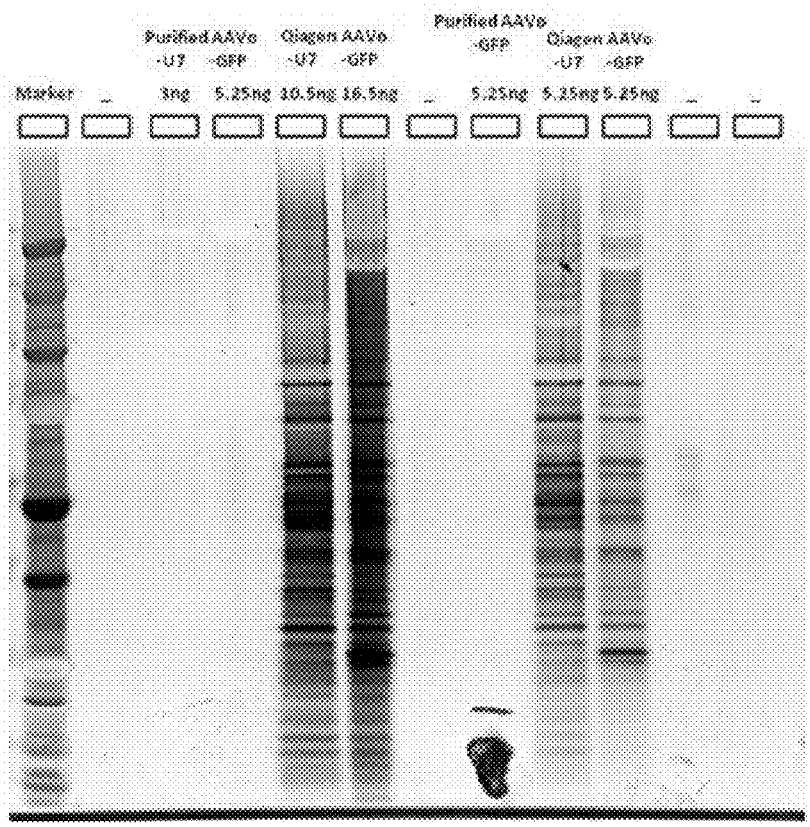

FIG. 10 is a 4-12% gradient SDS-polyacrylamide gel showing protein contents in AAVo samples after purification by either a commercial DNA purification device (Qiagen Plasmid Plus Maxi kit, Qiagen AAVo) or our chromatography system (purified AAVo). Different amounts of AAVo encoding either GFP or U7 were loaded onto a 4-12% gradient SDS-polyacrylamide gel and separated by electrophoresis. Proteins were revealed by silver staining. Note that no protein contaminants could be detected after purification by using our chromatography procedure.

DETAILED DESCRIPTION OF THE INVENTION

The present invention provides an isolated linear nucleic acid molecule comprising in this order: a first adeno-associated virus (AAV) inverted terminal repeat (ITR), an expression cassette of an exogenous DNA and a second AAV ITR, wherein said nucleic acid molecule is devoid of AAV capsid protein coding sequences. The nucleic acid molecule of the present invention is a rAAV vector devoid of capsid proteins (rAAV0), and may be used for the delivery of a desired exogenous DNA sequence for in vitro, ex vivo, or in vivo use of the same.

All publications, patents, and patent applications cited herein, whether supra or infra, are hereby incorporated by reference in their entirety.

The practice of the present invention will employ, unless otherwise indicated, conventional methods of virology, microbiology, molecular biology and recombinant DNA techniques within the skill of the art. Such techniques are explained fully in the literature. See, e.g., Sambrook, et al. *Molecular Cloning: A Laboratory Manual* (Current Edition); *DNA Cloning: A Practical Approach*, vol. I & II (D. Glover, ed.); *Oligonucleotide Synthesis* (N. Gait, ed., Current Edition); *Nucleic Acid Hybridization* (B. Hames & S. Higgins, eds., Current Edition); *Transcription and Translation* (B. Hames & S. Higgins, eds., Current Edition); *CRC Handbook of Parvoviruses*, vol. I & II (P. Tijssen, ed.); *Fundamental Virology*, 2nd Edition, vol. I & II (B. N. Fields and D. M. Knipe, eds.)

The various compositions and methods of the invention are described in detail below. Although particular compositions and methods are exemplified herein, it is understood that any of a number of alternative compositions and methods are applicable and suitable for use in practicing the invention.

Definitions

Unless otherwise indicated, all terms used herein have the same meaning as they would to one skilled in the art, and the practice of the present invention will employ conventional techniques of microbiology and recombinant DNA technology, which are within the knowledge of those of skill in the art.

The term "AAV0" as used herein refers to a capsid-less AAV vector construct containing the ITRs and any desired cargo, e.g., an exogenous gene or other polynucleotide and a promoter, but not the capsid. In a preferred embodiment, the capsid-less AAV vector construct does not contain sequences encoding the AAV Rep proteins. Thus, the term "AAV0 vector" or "recombinant AAV0 vector ("rAAV0")" as used herein refers to a capsid-less AAV construct that comprises, as minimal components, two ITRs and an exogenous DNA sequence to be transferred to a host operably linked or not to control elements. There is no requirement that all ITRs originate from one type of AAV. The terms "AAV0 vector", "rAAV0 vector" and "nucleic acid molecule of the invention" are herein used interchangeably.

The term "AAV0-plasmid" as used herein refers to a circular double-stranded DNA that encodes the rAAV0 vector, is capable of amplification in bacterial cells (i.e., has a selection marker allowing for growth of bacteria that have been transformed with the plasmid), and is introduced into a host cell for purposes of generating the rAAV0 vector itself, which is either a linear single- or eventually double-stranded DNA.

The term "inverted terminal repeats" or "ITRs" as used herein refers to AAV viral cis-elements named so because of their symmetry. These elements are essential for efficient multiplication of an AAV genome. It is hypothesized that the minimal defining elements indispensable for ITR function are a Rep-binding site (RBS; 5'-GCGCGCTCGCTCGCTC-3' for AAV2) and a terminal resolution site (TRS; 5'-AGTTGG-3' for AAV2) plus a variable palindromic sequence allowing for hairpin formation. According to the present invention, an ITR comprises at least these three elements (RBS, TRS and sequences allowing the formation of an hairpin). In addition, in the present invention, the term "ITR" refers to ITRs of known natural AAV serotypes (e.g. ITR of a serotype 1, 2, 3, 4, 5, 6, 7, 8, 9, 10 or 11 AAV), to chimeric ITRs formed by the fusion of ITR elements derived from different serotypes, and to functional variant thereof. By functional variant of an ITR, it is referred to a sequence presenting a sequence identity of at least 80%, 85%, 90%, preferably of at least 95% with a known ITR, allowing multiplication of the sequence that includes said ITR in the presence of Rep proteins, and allowing the transduction of a cell without the need of a transfection aid (as shown in the examples).

The terms "administering," "introducing," or "delivering," as used herein refer to delivery of a plasmid or vector of the invention for recombinant protein or nucleotide expression to a cell or to cells and/or tissues and/or organs of a subject. Such administering, introducing, or delivering may take place in vivo, in vitro, or ex vivo. A plasmid for recombinant protein or polypeptide expression may be introduced into a cell by transfection, which typically means insertion of heterologous DNA into a cell by chemical means (e.g., calcium phosphate transfection, polyethyleneimine (PEI), or lipofection); physical means (electroporation or microinjection); infection, which typically refers to introduction by way of an infectious agent, i.e., a virus (e.g., bacculovirus expressing AAV Rep genes); or transduction, which in microbiology refers to stable infection of a cell with a virus or the transfer of genetic material from one microorganism to another by way of a viral agent (e.g., a bacteriophage). A vector according to the invention for recombinant polypeptide, protein, or oligonucleotide expression may be delivered by physical means (e.g., calcium phosphate transfection, electroporation, microinjection or lipofection), or by preparing the vector with a pharmaceutically acceptable carrier for in vitro, ex vivo, or in vivo delivery to a cell, tissue, organ, or a subject. Furthermore, an AAV0 vector of the invention can enter cells without the aid of physical means or a carrier.

The terms "oligonucleotide" and "polynucleotide" usually refer to, respectively, generally smaller, nucleic acid fragments having from 4 to about 100 bases or generally larger (e.g., in excess of 100 bases and up to 30 kilobases) nucleic acid molecules and a sequence that is either complementary (antisense) or identical (sense) to the sequence of a messenger RNA (mRNA) or miRNA fragment or molecule. However, in this specification the terms are used interchangeably. Oligonucleotides can also refer to DNA or RNA molecules that are either transcribed or non-transcribed.

The term "central nervous system" or "CNS" as used herein refers to the art recognized use of the term. The CNS pertains to the brain, optic nerves, cranial nerves, and spinal cord. The CNS also comprises the cerebrospinal fluid, which fills the ventricles of the brain and the central canal of the spinal cord. Regions of the brain include, but are not limited to, the striatum, hippocampus, cortex, basal ganglia, subthalamic nucleus (STN), pedunculopontine nucleus (PPN), *substantia nigra* (SN), thalamus, putamen, or caudate regions of the brain, as well as the cerebellum, spinal cord or combinations thereof.

The term "concatamerize" or "concatemerize" as used herein refers to forming a polynucleotide molecule by linking sequences that repeat.

The term "control elements" as used herein refers to DNA sequences that are capable of directing or regulating the transcription of the exogenous DNA sequence upon delivery into a cell, tissue, and/or organ of a subject.

The term "converted double-strand form" as used herein refers to the final rAAV0 form which is operational in the host.

The term "exogenous DNA sequence" as used herein refers to a nucleic acid sequence that does not originate from the host in which it is placed. It may be identical to the host's DNA or heterologous. An example is a sequence of interest inserted into a vector. Such exogenous DNA sequences may be derived from a variety of sources including DNA, cDNA, synthetic DNA, and RNA. Such exogenous DNA sequences may comprise genomic DNA which may or may not include introns either naturally occurring or artificial. Moreover, such genomic DNA may be obtained in association with promoter regions or poly A signal sequences. The exogenous DNA sequences in the present invention can be cDNA. An exogenous DNA sequence includes without limitation any DNA sequence whose expression produces a gene product that is to be expressed in a host cell. The gene product may affect the physiology of the host cell. Exogenous DNA sequences also encompass DNA sequences that encode antisense oligonucleotides.

The term "exosome" as used herein refers to a vesicle made from one or more cell membrane proteins. Vesicles are normally produced in the endocytic-lysosomal system of a cell and are then expelled, secreted or "shed" by the cell. The term "microparticle" as used herein refers to membrane-ensheathed cell fragments carrying specific protein and RNA cargo (See EP Application 10306226.1).

The term "expression cassette" as used herein refers to an exogenous DNA sequence that is operably linked to a promoter or other regulatory sequence sufficient to direct transcription of the transgene. Suitable promoters include, for example, tissue specific promoters. Promoters can also be of AAV origin.

The term "gene delivery" or "gene transfer" as used herein refers to methods or systems for reliably inserting foreign nucleic acid sequences, e.g., DNA, into host cells. Such methods can result in transient expression of non-integrated transferred DNA, extra-chromosomal replication and expression of transferred replicons (e.g., episomes), or integration of transferred genetic material into the genomic DNA of host cells. Gene transfer provides a unique approach for the treatment of acquired and inherited diseases.

The term "genetic muscle disorder" as used herein refers to, but is not limited to, a neuromuscular or musculoskeletal disease or disorder, including without limitation, a neuromuscular disease caused by dominant mutation(s), recessive mutation(s), X-linked nuclear DNA mutation(s), or mitochondrial DNA mutation(s); also including large-range chromatin deletions which may or may not contain a gene but impacts gene editing. Examples include dominant or recessive limb girdle muscular dystrophies, Duchenne and Becker M D, Myotonic Dystrophy, Facioscapulohumeral dystrophy, and others.

The term "host cell" as used herein refers to, for example microorganisms, yeast cells, insect cells, and mammalian cells, that can be, or have been, used as recipients of rAAV vectors. The term includes the progeny of the original cell which has been transduced. Thus, a "host cell" as used herein generally refers to a cell which has been transduced with an exogenous DNA sequence. It is understood that the progeny of a single parental cell may not necessarily be completely identical in morphology or in genomic or total DNA complement to the original parent, due to natural, accidental, or deliberate mutation.

The term "neural cells" as used herein refers to cells that have been isolated from the brain, spinal cord or cells from any region of the central nervous system, as well as any cell present in the brain, spinal cord, or central nervous system of a subject. Examples of neural cells include neuronal cells, such as nerve cells that transmit nerve or chemical signals to and from the brain, such as sensory neurons or bipolar neurons that carry messages from the body's sense receptors (eyes, ears, etc.) to the CNS; motoneurons or multipolar neurons cells that carry signals from the muscles and glands to the CNS (e.g., spinal motor neurons, pyramidal neurons, Purkinje cells.); interneurons or pseudopolare cells which form the neural wiring within the CNS. These have two axons (instead of an axon and a dendrite). The term neural cells is also intended to include glial cells, which make up 90 percent of the brain's cells. Glial cells are nerve cells that do not carry nerve impulses. Types of glial cells include, but are not limited to, Schwann's cells, satellite cells, microglia, oligodendroglia, and astroglia.

The term "neurodegenerative disorder" or "neurological disorder" as used herein refers to a disorder which causes morphological and/or functional abnormality of a neural cell or a population of neural cells. The neurodegenerative disorder can result in an impairment or absence of a normal neurological function or presence of an abnormal neurological function in a subject. For example, neurodegenerative disorders can be the result of disease, injury, and/or aging. Non-limiting examples of morphological and functional abnormalities include physical deterioration and/or death of neural cells, abnormal growth patterns of neural cells, abnormalities in the physical connection between neural cells, under- or over production of a substance or substances, e.g., a neurotransmitter, by neural cells, failure of neural cells to produce a substance or substances which it normally produces, production of substances, e.g., neurotransmitters, and/or transmission of electrical impulses in abnormal patterns or at abnormal times. Neurodegeneration can occur in any area of the brain of a subject and is seen with many disorders including, for example, head trauma, stroke, ALS, multiple sclerosis, Huntington's disease, Parkinson's disease, and Alzheimer's disease.

The term "operably linked" as used herein relative to the rAAV0 vector means that nucleotide components of the rAAV0 vector are functionally related to one another for operative control of a selected coding sequence. Generally, "operably linked" nucleic acid sequences are contiguous, and, in the case of a secretory leader, contiguous and in reading frame. However, enhancers do not have to be contiguous.

The term "packaging" as used herein in the context of rAAV0 means including a genomic or other encoding sequence plus a control element (promoter), or a sense or antisense oligonucleotide sequence between two ITR elements. In most cases, the vector will have a control element, for example to drive transcription of U7 or RNAi or shRNA. In other cases, however, rAAV0 vectors can be used to deliver DNA that does not necessarily need to be transcribed and will thus lack the control element (e.g., a correcting matrix for zinc-finger or TAL exonuclease- or meganuclease-mediated gene repair).

The term "pharmaceutically acceptable" as used herein refers to molecular entities and compositions that are physiologically tolerable and do not typically produce toxicity or an allergic or similar untoward reaction, such as gastric upset, dizziness and the like, when administered to a human. Preferably, as used herein, the term "pharmaceutically acceptable" means approved by a regulatory agency of the Federal or a state government or listed in the U.S. Pharmacopeia or other generally recognized pharmacopeia for use in animals, and more particularly in humans.

The terms "polypeptide" and "protein" are used interchangeably herein and refer to a polymer of amino acids and includes full-length proteins and fragments thereof. As will be appreciated by those skilled in the art, the invention also includes nucleic acids that encode those polypeptides having slight variations in amino acid sequences or other properties from a known amino acid sequence. Amino acid substitutions can be selected by known parameters to be neutral and can be introduced into the nucleic acid sequence encoding it by standard methods such as induced point, deletion, insertion and substitution mutants. Minor changes in amino acid sequence are generally preferred, such as conservative amino acid replacements, small internal deletions or insertions, and additions or deletions at the ends of the molecules. These modifications can result in changes in the amino acid sequence, provide silent mutations, modify a restriction site, or provide other specific mutations. Additionally, they can result in a beneficial change to the encoded protein.

The term "purified" as used herein refers to material that has been isolated under conditions that reduce or eliminate the presence of unrelated materials, i.e. impurities, including native materials from which the material is obtained. For example, purified rAAV0 vector DNA is preferably substantially free of cell or culture components, including tissue culture components, contaminants, and the like. Exosomes or microparticles containing rAAV0 can be purified using specialized cell sorter machines which select for particles as small as 80 or even 60 µm. See EP 10306226.1.

The term "substantially free" is used operationally, in the context of analytical testing of the material. Preferably, purified material substantially free of impurities is at least 50% pure; more preferably, at least 90% pure, and more preferably still at least 99% pure. Purity can be evaluated by chromatography, gel electrophoresis, immunoassay, composition analysis, biological assay, and other methods known in the art.

The term "recombinant" as used herein refers to nucleic acids, vectors, polypeptides, or proteins that have been generated using DNA recombination (cloning) methods and are distinguishable from native or wild-type nucleic acids, vectors, polypeptides, or proteins.

The term "rescue" as used herein refers to release of the AAV0 genome from a duplex molecular form, e.g., either contained in a plasmid, heterologous virus genome (e.g., baculovirus), or a provirus in the cellular genome. The release and replication processes together are typically considered to comprise rescue. Several steps in the replication and release pathway were inferred from in vitro assays (Ward and Berns, 1991; Hong et al, 1992; Hong et al., 1994). Briefly, a recombination event occurs between the extruded duplex ITR resulting in a covalently closed-ended replication intermediate, previously referred to as "no-end" DNA (Ni et al., 1994). Either of the AAV p5 Rep proteins (Rep 78 or Rep 68) have sequence specific DNA binding and nicking activities and act on the closed-ended substrate. The Rep proteins bind to the stem region of the ITR and unwind the duplex DNA to expose the single strand nicking site, the terminal resolution site (trs). Either the Rep protein or cellular helicase activities unwind the ITR, thereby providing a 5'-overhang, ca.125 nt, and a free 3'-OH group that is extended by the cellular polymerase complex. A linear bimolecular duplex molecule is the product of terminal resolution events on either ends of the no-end intermediate. The bimolecular duplex DNA is now equivalent to annealed AAV genomes and replication may proceed indistinguishably for both rescued provirus DNA or virion-derived DNA.

The term "selectable marker" as used herein refers to a gene, introduced into a cell, which confers a trait suitable for selection, so as to indicate the success of a transfection or other procedure meant to introduce exogenous DNA into a cell. In general, anything that can be used as a detectable signal, either direct or indirect, is contemplated to be a selectable marker within the scope of the invention. Examples include, but are not limited to, a fluorescent marker such as GFP, a marker membrane peptide which allows for selection by cell sorting, and an antibiotic allowing for selection by resistance.

Antibiotics and metabolic selectable markers are routinely used for generating stable eukaryotic cell lines. For example, the antibiotic G418 is lethal to eukaryotic cells but is inactivated by the prokaryotic enzyme neomycin phosphotransferase. Similarly, hygromycin is toxic to mammalian cells, but is inactivated by hygromycin phosphotransferase. Chinese hamster ovary (CHO) cell lines have been developed lacking dihydrofolate reductase (DHFR). These cells are dependent on the exogenous glycine, hypoxanthine, and thymidine for survival. Accordingly, stable CHO cell lines can be generated by transfecting the desired transgene and DHFR in cis and culturing in HAT selective medium (reviewed in Hacker and Wurn, 2007).

The term "subject" as used herein includes, but is not limited to, humans, nonhuman primates such as chimpanzees and other apes and monkey species; farm animals such as cattle, sheep, pigs, goats and horses; domestic mammals such as dogs and cats; laboratory animals including rodents such as mice, rats and guinea pigs, and the like. The term does not denote a particular age or sex. Thus, adult and newborn subjects, as well as fetuses, whether male or female, are intended to be covered.

The term "therapeutic gene" as used herein refers to a gene that, when expressed, confers a beneficial effect on the cell or tissue in which it is present, or on a mammal in which the gene is expressed. Examples of beneficial effects include amelioration of a sign or symptom of a condition or disease, prevention or inhibition of a condition or disease, or conferral of a desired characteristic. Therapeutic genes include genes that partially or wholly correct a genetic deficiency in a cell or mammal.

The term "therapeutically effective amount" refers to an amount effective, at dosages and for periods of time necessary, to achieve the desired therapeutic result. A therapeutically effective amount of the recombinant vector may vary according to factors such as the disease state, age, sex, and weight of the individual and the ability of the vector to elicit a desired response in the individual. A therapeutically effective amount is also one in which any toxic or detrimental effect is outweighed by the therapeutically beneficial effects.

The term "tissue-specific promoter" as used herein refers to a promoter that is operable in cells of a particular organ or tissue, such as the central nervous system (CNS). Non-limiting examples of promoters for the CNS include but are not limited to, neuron-specific promoters (e.g., the neurofilament promoter; Byrne and Ruddle (1989) Proc. Natl. Acad. Sci. USA 86:5473-5477) and glial specific promoters (Morii et al. (1991) Biochem. Biophys Res. Commun. 175: 185-191). Preferably, the promoter is tissue specific and is essentially not active outside the central nervous system, or the activity of the promoter is higher in the central nervous system that in other systems. For example, a promoter specific for the spinal cord, brainstem, (medulla, pons, and midbrain), cerebellum, diencephalon (thalamus, hypothalamus), telencephalon (corpus stratium, cerebral cortex, or within the cortex, the occipital, temporal, parietal or frontal lobes), subthalamic nucleus (STN), *substantia nigra* (SN), or combinations, thereof. Other examples of promoters are the Chicken Beta Actin (CBA) promoter, neuron-specific enolase (NSE) promoter, creatine kinase promoter, desmin promoter, CAG promoter (composed of chicken b-actin promoter and CMV enhancer) (J. Miyazaki, 1989), liver-specific TBG promoter (2 copies of α-1 microglobulin/bikunin enhancer and thyroid hormone-binding globulin promoter) (Yang, 1997; Bell, 2011), CAG promoter (CMV enhancer/chicken β-actin promoter) coupled to TetOn/Tet-Off boxes (Lhériteau E, 2010), natural human U7 promoter (U.S. Provisional Application 61/314,830 and WO2006/021724, both of which are herein incorporated by reference in their entirety), promoter for cell-specific G protein-coupled receptor kinase 1 (Khani S C, 2007), and the like.

Muscle cell specific promoters are also known (Himeda et al., 2011). Nonlimiting examples are muscle-specific creatine kinase promoter, desmin promoter (Li et al., 1993), myosin light chain promoters (Cox et al., 1992), chimeric muscle specific promoters (Frauli et al., 2003) and troponin C promoter-enhancer (cardiac muscle).

The term "transfection" is used herein refers to the uptake of an exogenous nucleic acid molecule by a cell. A cell has been "transfected" when exogenous nucleic acid has been introduced inside the cell membrane. A number of transfection techniques are generally known in the art. See, e.g., Graham et al. (1973) Virology, 52:456, Sambrook et al.

(1989) Molecular Cloning, a laboratory manual, Cold Spring Harbor Laboratories, New York, Davis et al. (1986) Basic Methods in Molecular Biology, Elsevier, and Chu et al. (1981) Gene 13:197. Such techniques can be used to introduce one or more exogenous nucleic acid molecules into suitable host cells.

The term "vector" as used herein refers to any non-plasmid genetic element, such as a virus, rAAV0, AAV, parvovirus, virion, and the like.

As used herein, "ex vivo administration" refers to a process where primary cells or an entire organ are harvested from a subject, a rAAV0 vector is delivered into the cells, and the cells are readministered to the same or a different subject.

In the present description, any concentration range, percentage range, ratio range, or integer range is to be understood to include the value of any integer within the recited range and, when appropriate, fractions thereof (such as one tenth and one hundredth of an integer), unless otherwise indicated. Also, any number range recited herein relating to any physical feature, such as polymer subunits, size or thickness, are to be understood to include any integer within the recited range, unless otherwise indicated.

The term "about" or "approximately" means within a statistically meaningful range of a value. Such a range can be within an order of magnitude, preferably within 50%, more preferably within 20%, more preferably still within 10%, and even more preferably within 5% of a given value or range. The allowable variation encompassed by the term "about" or "approximately" depends on the particular system under study, and can be readily appreciated by one of ordinary skill in the art.

Further details of the invention are described in the following sections:

I. AAV0 Plasmid Construction and rAAV0 Vector Production

Viral capsids are in part responsible for the limited packaging capacity of AAV vectors. The lack of a capsid for the AAV0 vector bypasses this limitation and allows for a desired exogenous DNA sequence, even one substantially exceeding the packaging capacity of AAV in size, to be incorporated into the AAV0 vector and expressed upon introduction into a target cell, tissue, organ, or subject. For example, it is contemplated that inserts as large as 5, 8, 10 or 15 kb will be successfully transfected using the nucleic acid molecules (or rAAV0 vectors) of the present invention. Nucleotide sequences of the genomes of many AAV serotypes are known (NCBI: NC 002077; NC 001401; NC001729; NC001829; NC006152; NC 006260; NC 006261; Kotin and Smith, The Springer Index of Viruses, http://oesys.springer.de/viruses/database/mkchapter.asp-?virID=42.04). The AAV0 backbone of the present invention can be derived from the genome of any AAV serotype. Preferably, the AAV serotype is AAV2.

To date, the AAV genome itself has never been used or purified as a vector for gene therapy. That is, all known embodiments of AAV virus-mediated gene transfer to date involve the transfer of AAV viral particles encapsulated in AAV capsid proteins (e.g., Doenecke et al., 2010; Wang et al., 2011; Stieger et al., 2010; van der Marel S et al., 2011; Jiminez et al., 2011; White et al., 2011). While Doenecke et al reported plasmid AAV-mediated gene expression; this involved incorporating the AAV sequence into a bacterial plasmid. (As stated above, the plasmid backbone, however, is not suitable for rAAV0 production given its prokaryotic origin, which carries a significant risk of immunogenicity. Moreover, transfection of plasmids harboring AAV0 will result in mainly rescued rAAV0, with no or poor amplification.). The web site: http://www.ncbi.nlm.nih.gov/sutils/gmap.cgi?result=map&acc=NC_002077&organism=2397 also references various sequences of AAV but does not include one without a capsid. This is consistent with the view that a capsid-less AAV0 has not been contemplated.

Accordingly, the present invention relates to an isolated capsid-free AAV genome comprising an expression cassette for an exogenous DNA but devoid of capsid coding sequences. This corresponds to an isolated linear nucleic acid molecule comprising in this order: a first AAV ITR, an expression cassette of an exogenous DNA and a second ITR. In a particular embodiment of the invention, the nucleic acid molecule of the invention is a linear single-stranded or double-stranded nucleic acid. In a preferred embodiment, the nucleic acid molecule of the invention is single-stranded. In a first variant of this preferred embodiment, the first ITR is located at the 5' end of the nucleic acid molecule. In a second variant of this preferred embodiment, the second ITR is located at the 3' end of the nucleic acid molecule. In a third variant of this preferred embodiment, the first ITR is located at the 5' end and the second ITR is located at the 3' end of the nucleic acid molecule. In a particular embodiment, the isolated nucleic acid molecule backbone is derived from a known AAV genome such as one found in the above mentioned database. However, the isolated linear nucleic acid molecule of the invention may also be produced by genetic engineering by providing each element necessary for the construction of the vector, namely by providing two ITRs flanking an exogenous DNA expression cassette.

Of note, is that the present invention relates to a vector which is a nucleic acid molecule that is linear. Accordingly, it should be understood that the present invention does not correspond to an AAV plasmid. Indeed, plasmids are circular nucleic acid molecule of bacterial origin. In the present case, therefore, the present invention and a plasmid differ both in term of structure of the subject-matter (in particular, linear versus circular) and also in view of the methods used for producing and purifying these different objects (see below), and also in view of their DNA methylation which is of prokaryotic type for plasmids and of eukaryotic type for rAAV0.

Also of note, the rAAV0 vector (the nucleic acid molecule of the invention) differs from an AAV genome engineered into a different viral capsid such as that of a recombinant adenovirus (see for example WO 96/18727) because it is free of any viral capsid and has the capacity to be taken up into host cells directly without the interference of the host cell surface with a capsid protein, as well as to be transported from the cell cytoplasm into the nucleus without the interference of a capsid protein. In addition, the rAAV0 vector described herein does not elicit the immune response in a host elicited by an adenoviral capsid or indeed any other viral capsid used to package the AAV genome.

In one embodiment, the AAV0 backbone is derived from the AAV1, AAV2, AAV3, AAV4, AAV5, AAV6, AAV7, AAV8, AAV9, AAV10 or AAV11 genome. In a particular embodiment, the AAV0 backbone is derived from the AAV2 genome. In another particular embodiment, the AAV0 backbone is a synthetic backbone genetically engineered to include at its 5' and 3' ends ITRs derived from one or more of these AAV genomes. The two ITRs present in the nucleic acid molecule of the invention (i.e. in the rAAV0 vector) can be the same or different. In particular, they can be derived from the same AAV genome. In a specific embodiment, the two ITRs present in the nucleic acid molecule of the invention are the same, and can in particular be AAV2 ITRs.

rAAV0 plasmids (i.e., plasmids used for later producing the rAAV0 linear vector—see the definitions provided above) are constructed using known techniques to at least provide the following as operatively linked components in the direction of transcription: a 5' ITR; control elements including a promoter, an exogenous DNA sequence of interest; a transcriptional termination region; and a 3' ITR. Notably, the nucleotide sequences within the ITRs substantially replace the rep and cap coding regions. While rep sequences are ideally encoded by a helper plasmid or vector, it can alternatively be carried by the rAAV0 plasmid itself. In such cases, rep sequences are preferably located outside the region sandwiched between the ITRs, but can also be located within the region sandwiched between the ITRs. The desired exogenous DNA sequence is operably linked to control elements that direct the transcription or expression of an encoded polypeptide, protein, or oligonucleotide thereof in a cell, tissue, organ, or subject (i.e., in vitro, ex vivo, or in vivo). Such control elements can comprise control sequences normally associated with the selected gene. Alternatively, heterologous control sequences can be employed. Useful heterologous control sequences generally include those derived from sequences encoding mammalian or viral genes. Examples include, but are not limited to, promoters such as the SV40 early promoter; mouse mammary tumor virus LTR promoter; adenovirus major late promoter (Ad MLP); herpes simplex virus (HSV) promoters; a cytomegalovirus (CMV) promoter such as the CMV immediate early promoter region (CMVIE); a rous sarcoma virus (RSV) promoter; synthetic promoters; hybrid promoters; and the like. In addition, sequences derived from nonviral genes, such as the murine metallothionein gene, will also find use herein. Such promoter sequences are commercially available from, e.g., Stratagene (San Diego, Calif.). Alternatively, the promoter can be a tissue specific promoter. ITRs from any AAV serotype are suitable for use as 5' and 3' ITRs in the rAAV0 plasmids of the present invention, and ITRs from different AAV serotypes can be used for each of the 5' and 3' ITRs. ITR sequences of many AAV serotypes are known. For example, SEQ ID NOs: 1 and 2 are the ITR sequences for AAV2. SEQ ID NOs: 3-6 provide the genome sequences for AAV1, 3, 4, and 5, respectively. ITR sequences for these serotypes are known in the art. See for example, Chiorini, J A et al, 1997, J. Virol. 71(9): 6823-6833 Vol. 71, No. 9 which discloses ITR sequences for AAV2, AAV3 and AAV4.

rAAV0 plasmids can also include a selectable or selection marker for use in the establishment of a host cell rAAV0 vector producing cell line. The selection marker is operably linked to a promoter, for example, the *Orgyia pseudotsugata* immediate early-1 promoter (Op IE-1). In one embodiment, the selection marker can be inserted downstream (i.e., 3') of the 3' ITR. In another embodiment, the selection marker can be inserted upstream (i.e., 5') of the 5' ITR. Appropriate selection markers include, for example, those that confer drug resistance. Selection markers can be, for example, a blasticidin S-resistance gene, kanamycin, geneticin, and the like. In a preferred embodiment, the drug selection marker is a blasticidin S-resistance gene.

Suitable exogenous DNA sequences for use in rAAV0 plasmids and vectors are not limited in size due to the lack of a packaging constraint conferred by the viral capsid. As such, in some embodiments, the exogenous DNA sequence can exceed 5,000 bp, and in other embodiments, the exogenous DNA sequence can exceed 10,000 bp. In other words, an exogenous DNA sequence that exceeds the AAV packaging capacity by at least 10%, in fact by 20% and as large as 15 kb can be readily incorporated into AAV0 vectors. There are no specific requirements as to the identity of the exogenous DNA sequence for use in the present invention. Exogenous DNA sequences include, for example, a gene that encodes a protein that is defective or missing from a recipient subject or a gene that encodes a protein having a desired biological or therapeutic effect (e.g., an antibacterial, antiviral or antitumor function). In other embodiments, the exogenous DNA sequence will encode a gene product that can function to correct the expression of a defective gene or transcript (e.g., modified U7, meganuclease, transsplicing cassette, or to modulate post-transcriptional processing mechanisms (e.g., splicing)). The exogenous DNA sequence preferably encodes a protein that is relevant to the tissue to which it is administered. Exogenous DNA sequences can also encode corrective DNA strands, encode polypeptides, sense or antisense oligonucleotides, or RNAs (coding or non-coding; e.g., siRNAs, shRNAs, micro-RNAs, and their antisense counterparts (e.g., antagoMiR)).

Suitable exogenous DNA sequences include, but are not limited to, those encoding for polypeptides, proteins, or oligonucleotides used for the treatment of endocrine, metabolic, hematologic, hepatic, cardiovascular, neurologic, musculoskeletal, urologic, pulmonary and immune disorders, including such disorders as inflammatory diseases, autoimmune, chronic, infectious, and genetic diseases, such as Duchenne muscular syndrome, Spinal muscular atrophy (SMA), AIDS, cancer (especially solid tumors), hypercholestemia, insulin disorders such as diabetes, growth disorders, various blood disorders including various anemias, thalassemias and hemophilia; genetic defects such as cystic fibrosis, Gaucher's Disease, Hurler's Disease, adenosine deaminase (ADA) deficiency, emphysema, Pompe disease, progeria, Parkinson's disease, Huntington disease, Alzheimer disease, ALS, epilepsy, stroke, and the like.

Suitable transgenes to be encoded by the rAAV0 vector include, for example, dystrophin; LARGE (Barresi et al., 2004); dysferlin; calpain 3; Dux 4; LAMA2; α-, β-, γ-, and δ-sarcoglycan; FKRP, fukutin, WASP, factor VIII, factor IX, SMN1, U7, U1, RdCVF (Léveillard et al., 2010), α-glucosidase, LAMIN A/C, ZMPSTE 4, and actin. In principle, any gene that encodes a protein or polypeptide that is either reduced or absent due to a mutation or which conveys a therapeutic benefit when overexpressed is considered to be within the scope of the invention.

Also contemplated within the scope of the invention is the use of U7 technology to skip a gene out of frame (Pietri-Rouxel et al., 2010; U.S. Provisional Application 61/314,830 and WO2006/021724, herein incorporated by reference in their entirety. In this way, the expression of any gene can be regulated. In this context, the expression of genes in which the mutated version is known to be responsible for a disease, but not essential for the normal functioning of an organism or organ (e.g., SOD1, DM1), can be reduced via the U7 system. The U7 system can also be used for gene correction via trans-splicing (U.S. Provisional Patent Application No. 61/249,702 incorporated by reference in its entirety and EP2010/065142, which is also amenable for use with the rAAV0 vector system. Importantly, the rAAV0 technology also allows for the parallel (i.e., decoupled) downregulation of a gene (e.g., a gene carrying a dominant mutation) and substitution of the same gene (to restore its physiological properties). In this manner, one rAAV0 vector is used to shut down a gene and another to introduce a normal copy of the same gene, reducing or eliminating interference of one with the other and permitting independent dosing of the two interventions. Such an approach can use e.g., out-of-frame exon skipping for gene silencing (Id.) using one rAAV0 vector encoding an exon-skipping inducing AON and introduce a normal gene copy with a second rAAV0 vector, wherein codon optimization renders the normal gene copy insensitive to the oligoantisense sequence introducing the exon skipping (see, for example, Dominguez et al., 2010 and Millington-Ward et al., 2011). In this context, it is also important that the two vectors can be dosed, and repeatedly, in an independent way, thereby allowing for adjustment of desired expression levels in the target tissue. In yet another embodiment, different rAAV0 vectors can be introduced in parallel to substitute, simultaneously or consecutively, different isoforms of a gene.

The invention further provides a method for the production of a rAAV0 vector, comprising:

providing a host cell with a rAAV0 plasmid as described above, wherein both the host cell and the plasmid are devoid of capsid protein encoding genes, culturing the host cell under conditions allowing production of an AAV0 genome, harvesting the cells and isolating the AAV0 genome produced from said cells.

In the above method, conditions allowing production of an AAV0 genome are particularly those comprising the induction of Rep protein expression, as is provided below.

rAAV0 vectors have been successfully isolated using plasmid purification kits appropriately scaled for the quantity of cells. For example, the Qiagen EndoFree Plasmid kits have been used to isolate and purify rAAV0 from SD cells. Other methods developed for plasmid isolation may be adapted for rAAV0 since the principle is the same, i.e., fractionating low molecular weight DNA from cellular genomic DNA, and removing protein and RNA from the product.

Any cell line known in the art for producing AAV vectors can be used as a host rAAV0 vector producing cell line. In particular, cell types (e.g., SD, 293, and the like) in which AAV-REP proteins can be used for AAV0 genome mobilization are contemplated. Other cell lines known to be infected by AAV can also be used, such as Huh-7, HeLa, HepG2, Hep1A, 911, CHO, COS, MeWo, NIH3T3, A549, HT1180, monocytes, and mature and immature dendritic cells. For exemplary purposes only, we describe below the process of generating rAAV0 vectors using Sf9 insect cells.

rAAV0 plasmids can be introduced into Sf9 cells by transient transfection using reagents (e.g., liposomal, calcium phosphate) or physical means (e.g., electroporation) known in the art. Alternatively, stable Sf9 cell lines which have stably integrated the rAAV0 plasmids into their genomes can be established. Such stable cell lines can be established by incorporating a selection marker into the rAAV0 plasmid as described above.

Conventionally, AAV virions with capsids are produced by introducing a plasmid or plasmids encoding the rAAV genome, Rep proteins, and Cap proteins (Grimm et al., 1998). Upon introduction of these helper plasmids in trans, the AAV genome is "rescued" (i.e., released and subsequently recovered) from the host genome, and is further encapsidated to produce infectious AAV. However, such encapsidated AAV virus vectors were found to inefficiently transduce certain cell and tissue types. In contrast, transductions with capsid-less AAV0 vectors were unexpectedly found by the present inventors to be highly efficient for cell and tissues types that are difficult to transduce with conventional AAV virions. The present invention can be distinguished from such conventional methods in that only an AAV Rep encoding vector is required in trans. The AAV Rep encoding vector can be in the form of, for example, a bacculovirus expressing Rep proteins. As described above, Rep can be introduced by different means, e.g., via plasmid transfection, viral transduction, or stable integration in cell lines whereby expression is induced upon promoter activation. Thus, once the AAV Rep encoding vector is introduced into the Sf9 cell line that has stably integrated the rAAV0 plasmid into its genome, the rAAV0 vector is rescued from the host genome, but is not further encapsidated into virion particles. It is also possible for the rAAV0 plasmid to incorporate AAV Rep protein encoding nucleotide sequences.

Rescued rAAV0 vector can be purified in the form of DNA, using methods known in the art or using commercially available kits (e.g., Qiagen miniprep kit).

Rescued rAAV0 vector can also be purified in the form of exosomes, or microparticles. It is known in the art that many cell types release not only soluble proteins, but also complex protein/nucleic acid cargoes via membrane microvesicle shedding (Cocucci et al, 2009; EP 10306226.1). Such vesicles include microvesicles (also referred to as microparticles) and exosomes (also referred to as nanovesicles), both of which comprise proteins and RNA as cargo. Microvesicles are generated from the direct budding of the plasma membrane, and exosomes are released into the extracellular environment upon fusion of multivesicular endosomes with the plasma membrane. Thus, rAAV0 vector-containing microvesicles and/or exosomes can be isolated from cells that have been transduced with the rAAV0 vector. Microvesicles can be isolated by subjecting culture medium to filtration or ultracentrifugation at 20,000 g, and exosomes at 100,000 g. The optimal duration of ultracentrifugation can be experimentally-determined and will depend on the particular cell type from which the vesicles are isolated. Preferably, the culture medium is first cleared by low-speed centrifugation (e.g., at 2000 g for 5-20 minutes) and subjected to spin concentration using, e.g., an Amicon spin column (Millipore, Watford, UK). Microvesicles and exosomes can be further purified via FACS or MACS by using specific antibodies that recognize specific surface antigens present on the microvesicles and exosomes. Other microvesicle and exosome purification methods include, but are not limited to, immunoprecipitation, affinity chromatography, filtration, and magnetic beads coated with specific antibodies or aptamers. Upon purification, vesicles are washed with, e.g., phosphate-buffered saline. One advantage of using microvesicles or exosomes to deliver rAAV0 vesicles is that these vesicles can be targeted to various cell types by including on their membranes proteins recognized by specific receptors on the respective cell types. (See also EP 10306226.1)

As mentioned above, the host cell for rAAV0 vector production is not limited to Sf9 cells. In some embodiments, cells isolated from a subject afflicted with a disease can be used as hosts for rAAV0 vector production. In a preferred embodiment, the cells can be isolated from tissue that is specifically affected by the disease. For example, muscle cells can be isolated from subjects suffering from muscular dystrophy. In some cases, the rAAV0 vector-transduced host cell (e.g., cultured myoblasts) will actively shed exosomes and/or microparticles comprising the rAAV0 vector. These exosomes and/or microparticles can then be harvested as tissue culture supernatant and used for subsequent vector transduction. In one example, the exosome and/or microparticle-containing culture supernatant can be used to deliver rAAV0 vector into retinal cells to treat for example, RPGRIP1 deficiency (Lhériteau et al., 2009) or retinitis pigmentosa (Ji-jing Pang et al., 2008). For a review, see Rolling et al., 2010.

In a particular embodiment, the method for the production of a rAAV0 vector comprises the steps of:
- transfecting insect cells (in particular Sf9 cells) with a plasmid containing the AAV0 construct,
- optionally, establishing a clonal cell line using a selection marker present on the plasmid,
- introducing a Rep coding gene (either by transfection or infection with a baculovirus carrying said gene) into said insect cell,
- harvesting the cell and purifying the rAAV0 vector.

Purification can in particular be implemented by submitting a cell pellet to an alkaline lysis, centrifuging the lysate and loading the supernatant on an ion exchange column (e.g. Sartobind Q) which retains nucleic acids. The material is then eluted (e.g. with a 1.2 M NaCl solution) and loaded on a gel filtration column (e.g. 6 fast flow GE). The AAV0 vector is then recovered by precipitation.

Thanks to the production method of the present invention, high amounts of rAAV0 vector can be produced.

In another example, rAAV0 vectors can be used to transfect stem cells in vitro. These can be any kind of stem cell, e.g., embryonic stem cells, induced pluripotent stem cells, adult stem cells, and circulating or tissue-resident stem cells. Examples include, but are not limited to, CD 133+ cells, mesangioblasts, and ALDH+ stem cells. These stem cells can be cultivated ex vivo and transduced by rAAV0 vectors to elicit transient or permanent modification of gene expression. Transient modification can be achieved by transduction of DNA or RNA sequences capable of inducing, silencing, or modifying gene expression either by introducing a gene coupled to a functional promoter or by introducing a U1 or U7 gene coupled to antisense-sequences capable of inducing an exon skipping event (in frame or out of frame) or by conferring trans-splicing sequences. If transduction is carried out during an early passage stage of cell culture, the rAAV0 vector will be diluted through subsequent passages and eventually be lost, i.e., this will result in transient modification of gene expression. In contrast, if DNA-cutting enzymes are encoded by the transferred gene, such as zinc-finger nucleases or meganucleases or TAL exonucleases, this can result in permanent (Mendelian) gene modification of the recipient cell. A particular advantage of AAV0 technology in this context is that due to the ability to incorporate sequences larger than that allowed by conventional AAV vectors as well as the possibility of transfection with one or multiple AAV0 vectors containing complementary cargo, a correction DNA matrix can be simultaneously transferred into these cells.

II. Administration of rAAV0 Vectors

The cells to which the rAAV0 vectors are delivered into can be derived from a human, and other mammals such as primates, horse, sheep, goat, pig, dog, rat, and mouse. rAAV0 vectors can be delivered to any cell type, tissue, or organ without limitation. Examples of cells to which rAAV0 can be delivered into include, but are not limited to, cells of the central nervous system (CNS), cells of the peripheral nervous system (PNS), muscle cells, osteoblasts, tumor cells, lymphocytes, and the like. Examples of tissues and organs to which rAAV0 vectors can be delivered to include muscle, cardiac muscle, smooth muscle, brain, bone, connective tissue, heart, kidney, liver, lung, lymph node, mammary gland, myelin, prostate, testes, thymus, thyroid, trachea, and the like. Preferred cell types are muscle cells, cells of the CNS, and cells of the PNS. Preferred tissue and organs are muscle, heart, eye, and brain.

Depending on the particular tissue in which the target cell type resides, tissue-specific expression of a DNA, RNA, polypeptide, protein, or AON of interest can be achieved by incorporating a tissue-specific promoter that drives the transcription of the exogenous DNA sequence in the rAAV0 vector. Examples of tissue-specific promoters are as set forth previously.

rAAV0 vectors of the invention can be delivered to a cell by any means, including contacting the rAAV0 vector with the cell. That is, rAAV0 vectors do not absolutely require a transfection reagent for cell entry. This is a highly unexpected property since according to a classical hypothesis in this field, transduction by an AAV particle includes the endocytosis of the AAV particle, its intracellular trafficking to the nucleus and its nuclear import (see for example Ding et al., 2005). The encapsidated AAV genome is then released in the nucleus from the AAV particle. According to this view, the person skilled in the art would have expected that using a capsid-less AAV genome would have lead to no transduction of the cells because of an inability to either enter the cell or to translocate into the nucleus, or to a likely degradation of the genome by endonucleases or exonucleases. Contrary to this dogma, the present inventors have shown that a capsid-less AAV0 genome is able to transduce a cell, and to reach the nucleus in a functional form from which gene expression could be achieved.

The invention thus also relates to a method for the delivery of a nucleic acid of interest in a cell, comprising contacting at least one rAAV0 vector with the cell's surface in the absence of a transfection agent or additional physical means to facilitate entry of said rAAV0 vector into the cell. It also relates to a method for effecting the expression of a desired gene product or oligonucleotide in a cell comprising contacting at least one rAAV0 vector with the cell's surface in the absence of a transfection agent or additional physical means to facilitate entry of said rAAV0 vector into the cell.

rAAV0 vectors can present an alternative to transfection reagent-based delivery of genetic material into cells. In some embodiments, however, rAAV0 vectors can be used in conjunction with transfection reagents or physical means to facilitate entry into cells. In vitro, the rAAV0 vectors can be delivered into a cell by methods known in the art for delivering DNA into cells. For example, rAAV0 vectors can be introduced into cells by standard transfection methods (e.g., transfection reagents such as liposomes, alcohols, polylysine-rich compounds, arginine-rich compounds and calcium phosphate), microinjection, and the like. Other methods of introduction into cells include, for example, conjugation to proteins, nanoparticles, or packaging into cell-derived microvesicles (e.g., microparticles, exosomes) (See EP 10306226.1)

For in vivo delivery to cells, tissues, or organs of a subject, rAAV0 vectors can be incorporated into pharmaceutical compositions suitable for administration to a subject. Typically, the pharmaceutical composition comprises the rAAV0 vectors and a pharmaceutically acceptable carrier. As used herein, "pharmaceutically acceptable carrier" includes any and all solvents, dispersion media, coatings, antibacterial and antifungal agents, isotonic and absorption delaying agents, and the like that are physiologically compatible. Examples of pharmaceutically acceptable carriers include one or more of water, saline, phosphate buffered saline, dextrose, glycerol, ethanol and the like, as well as combinations thereof. Pharmaceutical compositions comprising rAAV0 vectors can be delivered as, for example, ageratum, sprays, oral suspensions, suppositories, eye drops, and injectable suspensions.

The rAAV0 vectors of the invention can be incorporated into a pharmaceutical composition suitable for topical, systemic, intra-amniotic, intrathecal, intracranial, intraarterial, intravenous, intralymphatic, intraperitoneal, subcutaneous, tracheal, intra-tissue (e.g., intramuscular, intracardiac, intrahepatic, intrarenal, intracerebral), intrathecal, intravesical, conjunctival (e.g., extra-orbital, intraorbital, retroorbital, intraretinal), and mucosal (e.g., oral, rectal, nasal) administration. Passive tissue transduction via high pressure intravenous or intraarterial infusion, as well as intracellular injection, such as intranuclear microinjection or intracytoplasmic injection, are also contemplated.

Pharmaceutical compositions for therapeutic purposes typically must be sterile and stable under the conditions of manufacture and storage. The composition can be formulated as a solution, microemulsion, dispersion, liposomes, or other ordered structure suitable to high rAAV0 vector concentration. Sterile injectable solutions can be prepared by incorporating the rAAV0 vector compound in the required amount in an appropriate buffer with one or a combination of ingredients enumerated above, as required, followed by filtered sterilization.

For in vivo administration of rAAV0 vectors, broad distribution of the rAAV0 vectors can be achieved in muscle by, for example, intravenous, intra-arterial injection or hydrodynamic locoregional perfusion. Depending on dosage and mode of delivery, 20-95% of muscle fibres in a given target muscle can be transduced. Broad distribution of the rAAV0 vectors can also be achieved in the CNS or PNS by injecting the rAAV0 vector into the cerebrospinal fluid, e.g., by lumbar puncture (e.g., Kapadia et al., 1996). Alternatively, precise delivery of the vector into specific sites of the brain to target a neural cell, can be conducted using stereotactic microinjection techniques (Snyder-Keller et al., 2010). Particularly preferred delivery methods are those that deliver the rAAV0 vector to specific regions of the brain or muscle that require expression of a polypeptide, protein, or oligonucleotide encoded by the rAAV0 vector. Direct injection of rAAV0 vectors, whether subcutaneous, intracranial, intramuscular, or intradermal, can take place using standard needle and syringe methodologies, or by needle-free technologies. The methods above can be performed with the rAAV0 vectors in the form of pharmaceutical compositions comprising a pharmaceutically acceptable carrier or vehicle. Topical applications are also contemplated with or without cells, the latter using AAV0 directly on skin in a topical preparation for recessive forms of epidermolysis bullosa (see, e.g., Yan et al., 2010).

Further methods for delivery of nucleic acid molecules, such as the rAAV0 vectors of this disclosure, are described, for example, in Boado et al., *J. Pharm. Sci.* 87:1308-1315 (1998); Tyler et al., *FEBS Lett.* 421:280-284 (1999); Pardridge et al., *Proc. Nat'l Acad. Sci. USA* 92:5592-5596 (1995); Boado, *Adv. Drug Delivery Rev.* 15:73-107 (1995); Aldrian-Herrada et al., *Nucleic Acids Res.* 26:4910-4916 (1998); Tyler et al., *Proc. Nat'l Acad. Sci. USA* 96:7053-7058 (1999); Akhtar et al., *Trends Cell Bio.* 2:139 (1992); "Delivery Strategies for Antisense Oligonucleotide Therapeutics," (ed. Akhtar, 1995); Maurer et al., *Mol. Membr. Biol.* 16:129-140 (1999); Hofland and Huang, *Handb. Exp. Pharmacol* 137:165-192 (1999); and Lee et al., *ACS Symp. Ser.* 752:184-192 (2000). These protocols can be utilized to supplement or complement delivery of virtually any rAAV0 vector contemplated within this disclosure.

Appropriate doses will depend on the particular cell type, tissue, organ, or subject being treated. When administered to a subject, dose will depend on the particular mammal being treated (e.g., human or nonhuman primate or other mammal), age and general condition of the subject to be treated, the severity of the condition being treated, the particular therapeutic polypeptide, protein, or oligonucleotide in question, its mode of administration, among other factors. An appropriate effective amount can be readily determined by one of skill in the art.

A "therapeutically effective dose" will fall in a relatively broad range that can be determined through clinical trials and will depend on the particular application (neural cells will require very small amounts, while systemic injection would require large amounts). For example, for direct in vivo injection into skeletal or cardiac muscle of a human subject, a therapeutically effective dose will be on the order of from about 1 µg to 100 g of the rAAV0 vector. If exosomes or microparticles are used to deliver the rAAV0 vector, then a therapeutically effective dose can be determined experimentally, but is expected to deliver from 1 µg to about 100 g of vector.

For in vitro transfection, an effective amount of rAAV0 vector to be delivered to cells ($1\times10^6$ cells) will be on the order of 1 to 20 µg rAAV0 vector, preferably 5 to 15 µg, and more preferably 8 to 10 µg. Larger rAAV cargoes will require higher doses. If exosomes or microparticles are used, an effective in vitro dose can be determined experimentally but would be intended to deliver generally the same amount of vector.

Treatment may involve administration of a single dose or multiple doses. Subject may be administered more than one dose, in fact multiple doses as needed, because the rAAV0 vector does not elicit an anti-capsid host immune response due to the absence of a viral capsid. As such, one of skill in the art can readily determine an appropriate number of doses. The number of doses administered can, for example, be on the order of 1-100, preferably 2-20 doses.

III. Therapeutic Uses of rAAV0 Vectors rAAV0 vectors of the invention are particularly suitable for delivering exogenous DNA sequences encoding polypeptides, proteins, or non-coding DNA, RNA, or oligonucleotides to, for example, cells of muscles and the CNS of subjects afflicted by a muscular or CNS disease.

rAAV0 vectors of the invention are particularly useful for a number of neurological and neurodegenerative diseases which can benefit from the expression of a peptide or protein which is defective in the diseases or disorder, such that expression of the peptide or protein would result in amelioration of symptoms associated with the disease or disorder. Some examples of applicable diseases include, but are not limited to, Duchenne muscular dystrophy, Spinal Muscular Atrophy, AIDS, Pompe disease, Parkinson's disease, Huntington disease, Alzheimer disease, Gaucher's disease, Hurler's disease, adenosine deaminase (ADA) deficiency, emphysema, progeria, ALS, epilepsy, stroke, hypercholestemia, insulin disorders (e.g., diabetes), growth disorders, various blood disorders (e.g., anemias, thalassemias, hemophilia), genetic defects (e.g., cystic fibrosis), cancer (especially solid tumors), and the like.

In some embodiments, rAAV0 vectors can be used to correct the expression of an aberrant protein by targeting the underlying defective mechanism that gives rise to the aberrant protein responsible for the development of the disease. Aberrant splicing of the dystrophin gene can be corrected using rAAV0 vectors containing, for example, nucleotide sequences that encode for AONs, U7, or a trans-splicing cassette (See, for example, Goyenvalle et al., 2004; Lorain et al., 2010; and the patent applications WO2006/021724, U.S. Provisional Application 61/314,830, U.S. Provisional Patent Application No. 61/249,702, and EP 2010/065142, all of which are herein incorporated by reference) to affected muscle tissue. In other embodiments, a full-length dystrophin gene containing rAAV0 vector can be delivered to affected muscle tissue.

Many diseases that involve the expression of an aberrant gene product are candidates for AAV0-mediated gene therapy. For instance, gene therapy for Duchenne muscular dystrophy (DMD), which manifests due to a defective dystrophin gene product, involves replacement of the defective dystrophin gene with a functional dystrophin gene, so that affected muscles in a subject's body may be treated. Mutations in the dystrophin gene result in a failure to produce dystrophin in striated muscles. The extent of the mutations does not, however, directly correlate with the severity of the phenotype. Out-of-frame deletions or nonsense mutations that yield premature stop codons and subsequent abortion of translation result in dystrophin deficiencies characterized by severe phenotypes. In-frame deletions are usually responsible for a milder myopathy known as Becker muscular dystrophy (BMD).

Efficacy of AAV0 vector-mediated therapy can be confirmed by introducing the rAAV0 vectors expressing the transgene of interest into cells isolated from patients or animal models available in the art. There are two well-characterized genetic animal models for DMD. The mdx mouse harbors a non-sense mutation in exon 23 of the dystrophin gene, which precludes the synthesis of full-length, wild-type dystrophin protein. The mdx mouse displays a compensatory mechanism counteracting the degeneration, which could maintain the regeneration process to restore the mechanical damage. The mdx mouse does not exhibit all symptoms of DMD and its life span is almost normal. The GRMD (Golden Retriever Muscle Dystrophy) dog lacks functional dystrophin because of a splice site mutation in intron 6, which disrupts the reading frame. In GRMD, as with human DMD, the progressive degradation of fibers leads inexorably to skeletal musculature wasting with marked endomysial and perimysial fibrosis. Because of its DMD-like phenotype, GRMD remains the best available model for the evaluation of potential therapies for DMD.

Methods for delivering the rAAV0 vectors of the invention are, in general, identical to those used for conventional viral vectors (See, for example, Goyenvalle et al., 2004; Toromanoff et al., 2010; Lowery et al., 2010; Duque et al., 2009). Even though deprived of capsid, AAV0 vectors do not need a transduction aid to enter the cell or the nucleus. Accordingly, the invention also provides a method for the delivery of an exogenous DNA in a cell, tissue or organ, comprising contacting said cell, tissue or organ with a rAAV0 vector of the invention without use of a transduction aid.

In another example, rAAV0 vectors can be adopted to induce cell death by selective gene transfer in the context of cancer (See, for example, Gruber et al., 2011).

In addition, the invention provides a method for the delivery of a nucleic acid of interest in a cell of a subject in need thereof, wherein the method is non-immunogenic or with reduced immunogenicity, comprising the administration to said subject of a rAAV0 vector of the invention comprising said nucleic acid of interest. In addition, the invention provides a method for the delivery of a nucleic acid of interest in a cell of a subject in need thereof, comprising multiple administrations of the rAAV0 vector of the invention comprising said nucleic acid of interest. Since the rAAV0 vector of the invention does not induce an immune response, such a multiple administration strategy will not be impaired by the host immune system response against the rAAV0 vector of the invention, contrary to what is observed with encapsidated vectors.

The above disclosure generally describes the present disclosure, which is further described by the following examples. These specific examples are provided solely for purposes of illustration, and are not intended to limit the scope of this disclosure. Although specific targets, terms, and values have been employed herein, such targets, terms, and values will likewise be understood as exemplary and non-limiting to the scope of this disclosure.

EXAMPLES

Example 1

Construction of rAAV0 Plasmids for rAAV0 Vector Production

The AAV0-GFP plasmid ("pFBGR/Blas"), was constructed as follows. The blasticidin S gene (2784-3183 bp) along with the *Orgyia pseudotsugata* immediate early-1 promoter (Op IE-1; 2401-2692 bp) (Invitrogen, Inc.) and EM7 promoter (2707-2765 bp) in pIB/V5-His/CAT plasmid (Invitrogen Inc.) was amplified by high fidelity PCR using primer sequences 5'-ATAAGCTTACGCTCAGTGGAAV-GAAAAC-3' (SEQ ID NO:7) and 5'-ATAAGCTTGACGT-GTCAGTGTCAGTCCTGCTCCT-3' (SEQ ID NO:8). After Hind III digestion, the 865 bp PCR product was cloned into the Hind III site of the AAV2 packaging plasmid, pFBGR (Urabe et al., 2002). Restriction mapping and DNA sequencing were carried out to confirm correct plasmid construction.

Example 2

Production and Purification of rAAV0 Vectors

Clonal Sf9 cell lines were established for the pFBGR/Blas plasmid. Spodoptera frugiperda (Sf-9) cells were transfected with the pFBGR/Blas plasmid using Cellfectin (Invitrogen). Following transfections, cells were incubated for 3 days at 27° C. in insect cell culture medium (HyClone Inc.). Blasticidin S HCl (50 µg/ml) was then added to select for stable transformants. After a two-week selection period, dilution cloning and direct colony transfer techniques were used to obtain independent clonal cell lines. Transformed cells were cultured and expanded in 10% FBS HyQ growth medium to form distinct colonies under Blasticidin S HCl selection (10 µg/ml).

Blasticidin-resistant clonal cell lines were individually infected with recombinant baculovirus expressing AAV Rep 78 and Rep 52 ("Rep-Bac") proteins (MOI=5) and screened for GFP expression. The Rep-Bac was as described in Urabe et al., 2002. The recombinant baculovirus was produced to generate sufficient quantities for animal studies as described in Virag et al., 2009. Following Rep-Bac infection, many cell lines were found to express GFP under fluorescence microscopy and also by flow cytometry (Guava EasyCyte). Extrachromosomal DNA was extracted from the Rep-Bac cells and analyzed by agarose gel electrophoresis. The presence of a 2.6 kb band after Rep-Bac infection indicated that the "provirus" rAAV0-GFP genome was "rescued" from the chromosomal DNA and replicated as AAV DNA at a high copy number.

For isolating and purifying AAV0 vectors, the clonal SD cell lines were expanded and seeded at $2\times10^6$ cells/mL at the time of infection with Rep-Bac (MOI=1 to 3). Cell viability and size were monitored daily (Cellometer). An increase in cell diameter is an indication of successful baculovirus infection. AAV0 vectors were harvested once the mean cell diameter reached 17-20 µm. Confirmation of GFP expression by fluorescence microscopy and Guava EasyCyte (Millipore) indicated efficient Rep baculovirus infection of Sf9/ITR-GFP cells. AAV0-GFP vector DNA extraction was performed with a Qiagen miniprep kit from cultured cells (1 mL) to confirm the presence of AAV0-GFP vector DNA. Larger scale DNA extraction can be carried out using a Qiagen gigaprep kit.

Example 3 rAAV0 Vector-Mediated Gene Expression In Vitro

Microinjection of rAAV0-GFP vector into nuclei or cytoplasm of 293 cells and C2C12 cells was carried out using a Xenoworks microinjection system (Sutter Instruments). Tetramethylrhodamine 70,000 MW lysine-fixable dextran was co-microinjected as an area marker of microinjection. Nuclei were stained with DAPI.

Furthermore, in order to demonstrate additional properties of rAAV0 compared to regular plasmid-DNA, the ability of rAAV0 to transduce cells when microinjected into the cytoplasm was tested. Indeed, plasmid-DNA needs to be delivered directly into the nucleus and cytoplasmic microinjections are not effective. Here, C2C12 myoblasts were grown and differentiated for 2 days. Microinjections of a solution (0.02 mg/ml) of AAV0-GFP vector into nuclei or cytoplasm of C2C12 myotubes were carried out using a Xenoworks microinjection system (Sutter Instruments). Tetramethylrhodamine 70,000 MW lysine-fixable dextran (Sigma) was also co-microinjected as an area marker of microinjection. 48 hours after microinjections, myotubes were fixed using paraformaldehyde 3.7% (Sigma) and permeabilized with 0.5% triton. All fluorescent stainings were mounted in Fluoromont G (Southern Biotech). Nuclei were stained using DAPI (Sigma). Fluorescent images shown in FIG. 5 were acquired using a Nikon Ti microscope equipped with a CoolSNAP HQ2 camera (Roper Scientific), using a 40×1.0 NA PL APO oil objective, driven by Metamorph (Molecular Devices). See FIG. 5b.

The results (left panels) in FIG. 5b show that cell nuclei became stained by fluorescent dye, which in turn indicates that the construct was delivered to the nucleus. GFP fluorescence confirmed GFP expression, which in turn indicates transcription from of the transduced rAAV0-GFP vector.

Example 4 rAAV0 Vector-Mediated Gene Expression In Vivo Via Intra-Arterial Injection

Intra-arterial injection of AAV0-GFP vector into the femoral artery was conducted by anesthetizing C57BL/6 mice, isolating the right hind limb for single manual, high-pressure injections, or both limbs for double manual high-pressure injections. After clamping the femoral vein and two collaterals, a catheter was introduced into the femoral artery and 100 of the AAV0-GFP vector preparation in 1 ml of phosphate-buffered saline (PBS) was injected at a rate of 100 ml/s. One minute after infusion, the femoral vein was unclamped ligated to open circulation. Limbs were analyzed for GFP expression 2 weeks after infusion.

Example 5 rAAV0 Vector-Mediated Gene Expression In Vivo does not Elicit an Immune Response Mice received two high powered intra-femoral injections of AAV0-GFP in one week intervals. The first injection was performed in the left leg (100 µg of AAV0-GFP in 1 ml of PBS), and the second a week later in the right leg (100 µg of AAV0-GFP in 1 ml of PBS). Mice were allowed to recover for 8 weeks after the second injection prior to analysis under a conventional Zeiss fluorescence microscope. Normally, re-administration of rAAV after >48 h is impossible due to the presence of neutralizing antibodies (Lorain et al., 2008). The fact that re-injection after 1 week results in undiminished contralateral leg transduction indicates absence of an immune response against the rAAV0 vector.

Example 6 rAAV0 Vector-Mediated Gene Expression Via Sub-Retinal Injection

For retro-orbital injections, animals will be anesthetized and injected with a solution containing 200 µg of AAV0-GFP vector in 400 µL of PBS into the retro-orbital sinus using, for example, an insulin syringe. In general, standard technologies will be applied for sub-retinal injections of mice or rats (Timmers et al., 2001) or dogs or non-human primates (Weber et al., 2003). rAAV0 vectors will contain a tissue-specific promoter such as the cell-specific G-protein-coupled receptor kinase 1 (GRK1) promoter, which is capable of establishing robust transgene expression in rod and cone photoreceptors (Khani et al., 2007). Another promoter example would be the ubiquitous smCBA promoter which efficiently targets the neural retina (Haire et al., 2006). These promoters can be linked as control elements to a desired transgene which is lacking expression in the disease to be treated, such as the guanylate cyclase-1 gene, mutations of which lead to Leber Congenital Amaurosis (Boye et al., 2010) or to the RPE 65 gene, also leading to Leber Congenital Amaurosis (Lhériteau et al., 2010), or to the RD 10 gene leading to recessive retinitis pigmentosa if mutated (Pang et al., 2011). For a review of retinal diseases amenable to a gene therapy approach, see Stieger and Lorenz, 2010. Typically, between 5×10e9 to 5×10e11 vector particles would be injected sub-retinally under general anesthesia in a species-adapted volume of 0.5-2 µl in the mouse or 50-600 µl in a dog or non-human primate. In larger animals, this approach can be combined with vitrectomy. Typically for a dog, a 44-gauge cannula (Corneal) would be connected to a viscous fluid injection (VFI) system (D.O.R.C. International, Netherlands) in order to deliver controlled and automated sub-retinal injection by inserting the cannula after sclerotomy through the vitreous and targeting the subretinal space underlying the tapetal central retina under microscopic control (Weber et al., 2003). Transgene expression would be studied functionally according to disease-specific visual function tests and biochemically by standard techniques (e.g., PCR, Western blot, Immunofluorescence). Efficacy can be determined as a measure of eye sight restitution using techniques known to one of ordinary skill in the art (e.g., vision tests, spatial orientation tests, electroretinography, visual evoked potentials). A measurable degree of restitution is expected to result.

Example 7 rAAV0 Vector-Mediated Gene Expression In Vivo Via Systemic Injection

Figure 1:
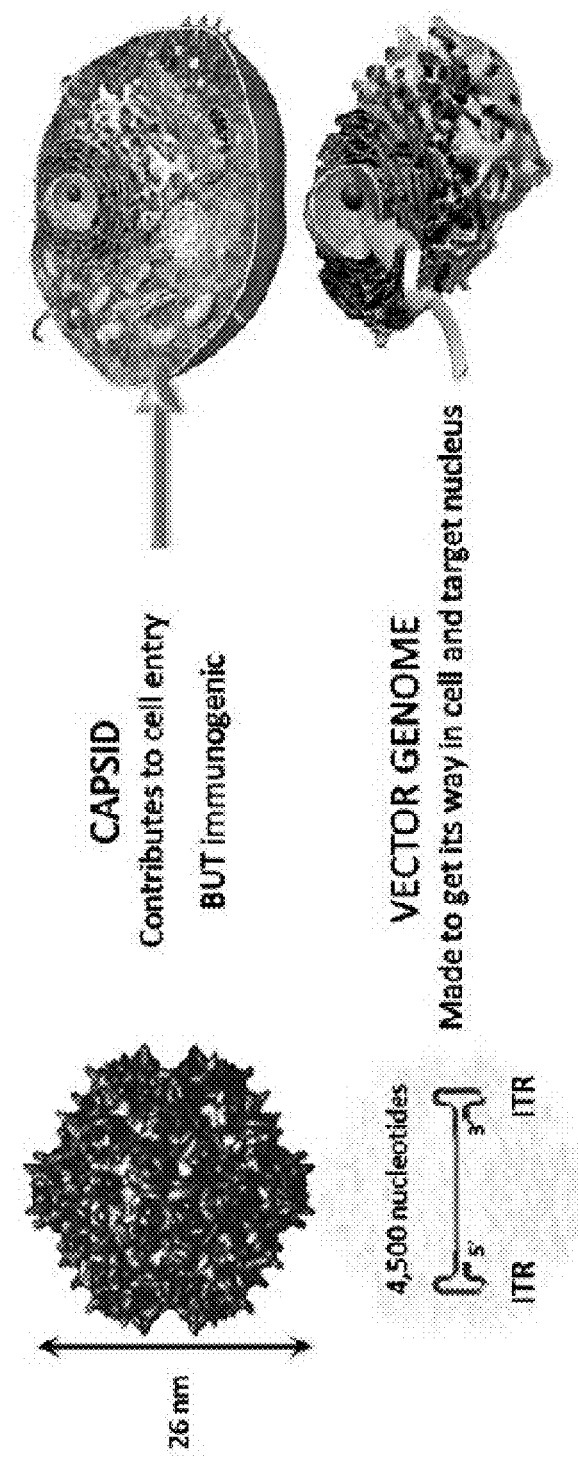
FIG. 1 is a schematic comparison of conventional AAV (capsid-containing) and rAAV0. While conventional AAV vectors (top) have two components, capsid and genome, the rAAV0 vectors (bottom) are capsid-less.
Figure 2:
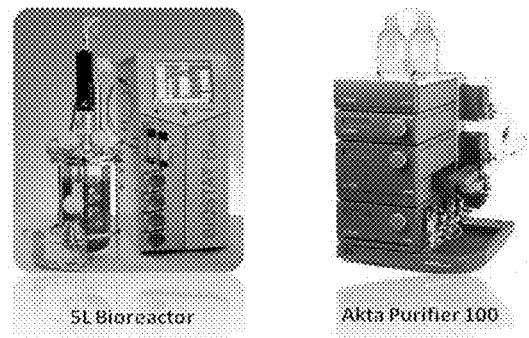
FIG. 2 is a scheme for rAAV0 vector synthesis and downstream applications.
Figure 2:
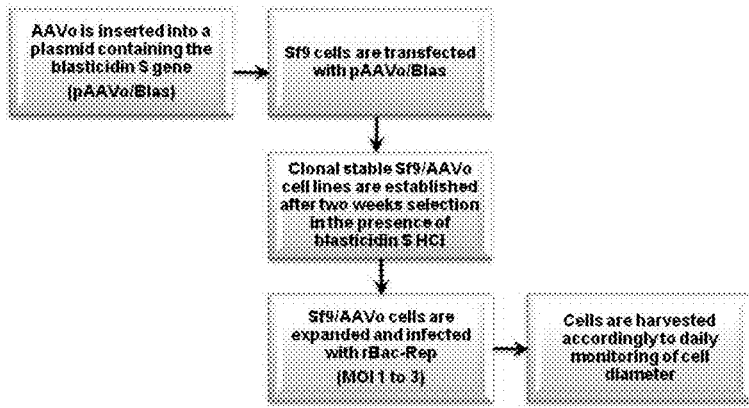
Figure 2:
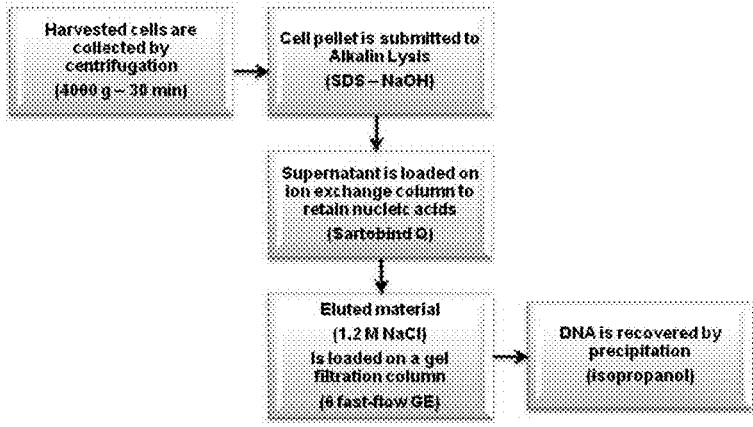

Mice (C57BL/6) will be administered rAAV0-GFP as described in Example 2 and FIG. 1 through tail-vein injections. AAV0-GFP preparation will consist of 100-200 μg of the rAAV0-GFP in 0.5 ml of phosphate-buffered saline (PBS). Tissues (e.g., muscles, heart, brain, liver, kidney) will be analyzed for GFP expression at different time points starting 2 weeks after the injection. It is anticipated that many, if not all, organs will be transduced.

Example 8

Exosome- and/or Microparticle-Mediated Delivery of rAAV0 Vector

The invention further provides for methods of treating a subject with Duchenne muscular dystrophy by (1) establishing a myoblast culture from a muscle biopsy of a subject with DMD, (2) transduce the myoblast culture with an rAAV0 vector encoding the DNA of interest, (3) collect exosomes or microparticles from the culture, and (4) introducing the collected exosomes or microparticles into the subject.

Myoblast cells cultured from a muscle biopsy of a subject with DMD are transduced with an rAAV0 vector encoding a DNA of interest. After an experimentally-determined duration of time, which would reflect optimal rAAV0-containing exosome or microparticle shedding from the host cell, culture supernatant is collected and first cleared at, for example, 20 minutes at 2000 g. The pre-cleared supernatant is then concentrated using a spin column (e.g., Amicon spin column; Millipore, Watford, UK) at 20,000 g for 70 minutes for microparticles and 100,000 g at 70 minutes for exosomes. The optimal duration of ultracentrifugation can be determined experimentally. Upon washing the ultracentrifuged pellet containing the microparticles or exosomes with, for example, PBS, the suspended pellet can be used directly or subjected to additional purification steps using antibodies against proteins known to be expressed on the surface of the vesicles by, for example, FACS, MACS, immunoprecipitation, affinity chromatography, or magnetic beads coated with specific antibodies or aptamers.

Purified rAAV0-containing microparticles or exosomes are then directly injected into the affected muscle tissue of the subject with DMD, or can be incubated with cultured stem cells isolated from the patient with DMD. In the latter case, the cultured stem cells that have internalized the microparticles or exosomes can be reintroduced into the affected tissue of the patient.

It is anticipated that microparticles or exosomes carrying rAAV0 vectors will be internalized, the vectors will enter the nucleus, and express the exogenous DNA.

Example 9

Generation of rAAV0-U7 Plasmid and Vector

The rAAV0-U7 plasmid and vector were generated in essentially the same manner as described in Example 1. Briefly, the full U7 snRNA gene (445 bp) was amplified by PCR from mouse genomic DNA using the following primers: 5'-TAACAACATAGGAGCTGTG-3'(SEQ ID NO:9) and 5'-CAGATACGCGTTTCCTAGGA-3' (SEQ ID NO:10). The Sm domain (AATTTGTCTAG; SEQ ID NO:11) was changed into smOPT (AATTTTTGGAG; SEQ ID NO:12) as described (SI), and the histone pre-mRNA pairing region was replaced by 44 bp complementary to: a) sequences across the branching point upstream of exon 23 of the dystrophin gene (BP22: 5'-AAATAGAAGTTCATTTACACTAAC-3'; SEQ ID NO:13) and b) sequences immediately adjacent to the exon 23 donor splice site (SD23: 5'-GGCCAAACCTCGGCTTACCT-3'; SEQ ID NO:14). The resulting U7smOPT-SD23/BP22 fragment was then introduced into the pFBGR/Blas plasmid to generate rAAV0-U7-smOPT-SD23/BP22 plasmid. Further details of the U7 snRNA construct can be found in commonly owned Provisional Patent Application 61/314,830 filed Mar. 17, 2010, incorporated by reference in its entirety. See also Goyenvalle et al., 2004.

Example 10

Therapeutic Use of rAAV0-U7 Vectors for Exon Skipping of Dystrophin In Vivo

The invention further provides for methods of treating a subject with Duchenne muscular dystrophy by either using intra-arterial injection of rAAV0-U7 into the femoral artery as described in Example 4 or systemic delivery as described in Example 6. Lack of immune response against the rAAV0 backbone also allows repeated treatments until levels of U7 in target tissues are clinically relevant as explained in Example 5. Therapeutic use will be assessed in the mdx mouse, a well-known mouse model of DMD, for which U7 tools have been developed that allow efficient dystrophin rescue by skipping exon 23 of the dystrophin pre-mRNA (Goyenvalle et al., 2004). Treated animals will be sacrificed at different time points after treatment and dystrophin rescue analyzed by RT-PCR (i.e., to determine skipping levels), Western blot, and immunofluorescence on tissue cryosections (as described in Goyenvalle et al., 2004) to determine protein synthesis and localization.

Example 11

Structural Characterization of the AAV0 Vector

An rAAV0 vector produced as mentioned previously has been submitted to a structural analysis using agarose gel (1%) electrophoresis (FIG. 8). The bands on the agarose gel (2.6 kbase) reflect the linear monomeric single-stranded structure of rAAV0 after DNA recovery at the end of the production process.

Electron microscopy of an rAVV0 vector in the presence of SSB (single stranded binding protein) has also been performed to confirm the single-stranded nature of the rAAV0 vector. AAV samples were diluted in 1× TE (10 mM Tris, 1 mM EDTA, pH 8) at approximately 15 ng/μl. 30 μl of the diluted samples were then incubated with 1 μl of 10 mg/ml T4 Gene 32 protein (which is a SSB protein), 15 minutes à 37° C. The samples were then purified on a Superose 6 filtration column previously equilibrated in 1× TE buffer to remove excess protein. The samples were then deposited on copper grids carbonated and functionalized with pentylamine. They were contrasted with uranyl acetate (positive staining) and observed under dark field transmission electron microscope (Zeiss 902). As shown in FIG. 9, rAAV0 appears as a linear structure, which is single stranded as revealed by SSB binding.

In order to assess protein contaminants in AAVo purified by either chromatography or Qiagen kits, rAAVo samples were separated on 4-12% SDS-PAGE (NuPAGE Tris-Acetate Mini Gels, Invitrogen) and silver stained stained (Silver Stain Plus, BioRad) for proteins.

Two types of rAAVo vectors were tested: AAVo(GFP) encoding GFP under the CMV promoter and AAVo(U7) harboring an expression cassette for a U7 snRNA. For each sample, different amounts of DNA were loaded on gel:

1: 15 µl at 200 ng/ml AAVo(U7)-purified
2: 15 µl at 350 ng/ml AAVo(GFP)-purified
3: 15 µl at 700 ng/ml AAVo(U7)-Qiagen
4: 5 µl at 3300 ng/ml AAVo(GFP)-Qiagen
5: 15 µl at 350 ng/ml AAVo(GFP)-purified
6: 7.5 µl at 700 ng/ml AAVo(U7)-Qiagen
7: 1.6 µl at 3300 ng/ml AAVo(GFP)-Qiagen.

The gel is represented on FIG. 10. No contaminant protein has been identified in purified rAAV0 samples. Therefore, the properties herein identified are only due to the rAAV0 vector itself, and not to helper proteins which would have been present in the sample.

While the disclosure has been described in each of its various embodiments, it is expected that certain modifications thereto may be undertaken and effected by the person skilled in the art without departing from the true spirit and scope of the disclosure, as set forth in the previous description and as further embodied in the following claims. The present disclosure is not to be limited in scope by the specific embodiments described herein. Indeed, various modifications of the disclosure in addition to those described herein will become apparent to those skilled in the art from the foregoing description and the accompanying figures. Such modifications are intended to fall within the scope of the appended claims. It is further to be understood that all values are approximate, and are provided for description.

All U.S. patents, U.S. patent application publications, U.S. patent applications, foreign patents, foreign patent applications, non-patent publications, figures, tables, and web sites referred to in this specification are expressly incorporated herein by reference, in their entirety.

Various Embodiments

1. A capsid-free adeno-associated viral vector (AAV0 vector) comprising two AAV inverted terminal repeats (ITRs) and an expression cassette, each of said ITRs having an interrupted palindromic sequence forming a hairpin structure, the cassette comprising at least one promoter operatively linked to an exogenous DNA, wherein:
   the expression cassette is flanked on each end by one inverted terminal repeat,
   the vector does not encode AAV capsid proteins, and the vector is not encapsidated.

2. The AAV0 vector of embodiment 1, wherein the exogenous DNA comprises from about 4,200 to about 15000 nucleotides.

3. The AAV0 vector of embodiment 1 wherein the exogenous DNA exceeds in length the packaging capacity of an encapsidated AAV vector.

4. The AAV0 vector of embodiment 1, wherein the exogenous DNA sequence encodes a protein.

5. The AAV0 vector of embodiment 1, wherein the exogenous DNA sequence encodes a sense or anti-sense oligonucleotide.

6. A method of producing a capsid-free adeno-associated viral (AAV0) vector comprising:

(a) providing cells comprising two AAV ITRs, an expression cassette positioned between the ITRs, said expression cassette comprising at least one promoter operatively linked to an exogenous DNA; wherein the expression cassette is flanked on each end by one inverted terminal repeat and does not encode AAV capsid proteins, and the cells do not express AAV capsid proteins;

(b) optionally providing into the cell AAV Rep genes or proteins, if not already present in the cells, but not AAV Cap genes or proteins;

(c) growing the cells under conditions permitting replication and release of DNA comprising the ITRs and the expression cassette and constituting AAV0 vector;

(d) collecting rescued AAV0 vector from the cells.

7. The method of embodiment 6 wherein the cells of step (a) further comprise a selection marker.

8. The method of embodiment 6, wherein the cell line is Sf9.

9. The method of embodiment 7, wherein the selection marker is a blasticidin S-resistance gene.

10. The method of embodiment 6 wherein the rescued AAV0 vector is collected as naked DNA or incorporated in exosomes or microparticles.

11. The method of embodiment 10 wherein the vector is collected as purified naked DNA.

12. The method of embodiment 10 wherein the vector is collected and purified in the form of microparticles or exosomes.

13. A method for mediating the expression of exogenous DNA in a mammalian cell comprising the steps of:

(a) delivering to the cell an effective amount of a capsid-free adeno-associated viral (AAV0) vector comprising two AAV inverted terminal repeats (ITRs) and an expression cassette, each of said ITRs having an interrupted palindromic sequence forming a hairpin structure, the cassette comprising at least one promoter operatively linked to the exogenous DNA, wherein (i) the expression cassette is flanked on each end by one inverted terminal repeat, (ii) the vector does not encode AAV capsid proteins, and (iii) the vector is not encapsidated; and (iv) the vector is not immunogenic.

(b) growing the cell under conditions permitting the expression by the cell of the exogenous DNA;

wherein the effective amount is sufficient to permit a desired level of expression by the cell of the exogenous DNA.

14. The method of embodiment 13 wherein the length of the exogenous DNA exceeds the packaging capacity of a conventional AAV vector comprising a capsid.

15. The method of embodiment 13 wherein the delivering comprises simply introducing the AAV0 vector in the extracellular medium and does not comprise use of any other transduction means.

16. The method of embodiment 14 wherein the exogenous DNA is from about 4.2 up to about 15 kb in length.

17. The method of embodiment 14 wherein the exogenous DNA is up to about 5 kb in length.

18. The method of embodiment 14 wherein the exogenous DNA is up to about 5 kb in length.

19. The method of embodiment 14 wherein the exogenous DNA is up to about 8 kb in length.

20. The method of embodiment 14 wherein the exogenous DNA is up to about 10 kb in length.

21. A method for mediating the expression of exogenous DNA in an organ or tissue of a mammal comprising the steps of:

(a) delivering to the mammal an effective amount of a capsid-free adeno-associated viral (AAV0) vector comprising two AAV inverted terminal repeats (ITRs) and an expression cassette, each of said ITRs having an interrupted palindromic sequence forming a hairpin structure, the cassette comprising at least one promoter operatively linked to the exogenous DNA, wherein (i) the expression cassette is flanked on each end by one inverted terminal repeat, (ii) the vector does not encode AAV capsid proteins, and (iii) the vector is not encapsidated (b) waiting for cells within said organ or tissue to elaborate the expression of the exogenous DNA;

wherein the effective amount is sufficient to permit a desired level of expression by the cells of the exogenous DNA.

22. The method of embodiment 21 wherein the delivering step comprises systemic delivery to said mammal.

23. The method of embodiment 21 wherein the length of the exogenous DNA exceeds the packaging capacity of a conventional AAV vector comprising a capsid.

24. The method of embodiment 23 wherein the exogenous DNA is from 4.2 up to about 15 kb in length.

25. The method of embodiment 22 wherein the systemic delivery comprises intra-arterial or intramuscular injection.

26. The method of embodiment 21, wherein the delivering step comprises sub-retinal injection.

27. The method of embodiment 25 wherein the AAV0 vector comprises a promoter directing the expression of said exogenous DNA preferentially or exclusively in a specific organ or tissue.

28. The method of embodiment 13 or 21 wherein the exogenous DNA encodes U7 snRNA.

29. The method of embodiment 13 or 21 wherein the exogenous DNA encodes RNAi or siRNA.

30. The method according to embodiment 13 wherein the delivering comprises the use of transfection reagents or physical means to facilitate entry into cells.

31. The method according to embodiment 13 wherein the delivering takes place in the absence of a transfection agent or additional physical means to facilitate entry of said rAAV0 vector into the cell.

32. A method for the treatment of a disease in a subject in need thereof, the disease involving a genetic defect manifesting symptoms due to reduced or ceased expression of a polypeptide or in expression of a nonfunctional or poorly functional analog of said polypeptide, the method comprising delivering to said subject an effective amount of a vector according to embodiment 1, wherein the exogenous DNA comprises an oligonucleotide or polynucleotide that skips, corrects, silences or masks the defect, resulting in amelioration of symptoms associated with the disease or disorder.

33. A method according to embodiment 32 comprising delivering to said subject an effective amount of a vector according to embodiment 1, wherein the exogenous DNA encodes RNAi, or siRNA or an antisense oligonucleotide or polynucleotide.

34. A method according to embodiment 32 comprising delivering to said subject an effective amount of a vector according to embodiment 1, wherein the exogenous DNA encodes an oligo or polynucleotide the expression of which would result in amelioration of symptoms associated with the disease by restoring at least partial function of said polypeptide.

35. A method for effecting the expression of a desired gene product or oligonucleotide in a cell comprising contacting at least one rAAV0 vector with the cell's surface in the absence of a transfection agent or additional physical means to facilitate entry of said rAAV0 vector into the cell.

36. A method for administering repeatedly to the same host a desired DNA or RNA sequence encoding, or not, specific proteins with one or more rAAV0 vectors without eliciting an immune response of the host against the rAAV0 vector.

37. The AAV0 vector of embodiment 1 wherein the single stranded linear DNA sequence has the capacity to be taken up into cells across the cell membrane, and to be transported from the cell cytoplasm to the nucleus, without interference by a viral capsid protein.

REFERENCES

Athanasopoulos T, Graham I R, Foster H, Dickson G. Recombinant adeno-associated viral (rAAV) vectors as therapeutic tools for Duchenne muscular dystrophy (DMD). Gene Ther. 2004 October; 11 Suppl 1:S109-21.

Barresi R, Michele D E, Kanagawa M, Harper H A, Dovico S A, Satz J S, Moore S A, Zhang W, Schachter H, Dumanski J P, Cohn R D, Nishino I, Campbell K P. LARGE can functionally bypass alpha-dystroglycan glycosylation defects in distinct congenital muscular dystrophies. Nat Med. 2004 July; 10(7):696-703.

Bell P, Gao G, Haskins M E, Wang L, Sleeper M M, Wang H, Calcedo R, Vandenberghe L, Weisse C, Withnall E, Wilson J M, Chen S J. Evaluation of AAV Vectors for Liver-directed Gene Transfer in Dogs. Hum Gene Ther. 2011 Jan. 4. [Epub ahead of print]

Benchaouir R, Meregalli M, Farini A, D'Antona G, Belicchi M, Goyenvalle A, Battistelli M, Bresolin N, Bottinelli R, Garcia L, Torrente Y. Restoration of human dystrophin following transplantation of exon-skipping-engineered DMD patient stem cells into dystrophic mice. Cell Stem Cell. 2007 Dec. 13; 1(6):646-57.

Berns, K. I., and C. R. Parrish. Parvoviridae, p. 2437-2477. In D. M. Knipe and P. M. Howley (ed.), Fields Virology, Fifth ed. Lippincott Williams and Wilkins, New York; 2007.

Bigot A, Jacquemin V, Debacq-Chainiaux F, Butler-Browne G S, Toussaint O, Furling D, Mouly V. Replicative aging down-regulates the myogenic regulatory factors in human myoblasts. Biol Cell. 2008 March; 100(3):189-99.

Boutin S, Monteilhet V, Veron P, Leborgne C, Benveniste O, Montus M F, Masurier C. Prevalence of serum IgG and neutralizing factors against adeno-associated virus (AAV) types 1, 2, 5, 6, 8, and 9 in the healthy population: implications for gene therapy using AAV vectors. Hum Gene Ther. 2010 June; 21(6):704-12.

Boye S E, Boye S L, Pang J, Ryals R, Everhart D, Umino Y, Neeley A W, Besharse J, Barlow R, Hauswirth W W. Functional and behavioral restoration of vision by gene therapy in the guanylate cyclase-1 (GC1) knockout mouse. PLoS One. 2010 Jun. 25; 5(6):e11306.

Cocucci E, Racchetti G, et al. Shedding microvesicles: artifacts no more. Trends Cell Biol. 2009 February; 19(2): 43-51.

Connelly J P, Barker J C, Pruett-Miller S, Porteus M H. Gene correction by homologous recombination with zinc finger nucleases in primary cells from a mouse model of a generic recessive genetic disease. Mol Ther. 2010 June; 18(6):1103-10.

Cox R D, Buckingham M E. Actin and myosin genes are transcriptionally regulated during mouse skeletal muscle development. Dev Biol. 1992 January; 149(1):228-34.

Cunningham S C, Spinoulas A, Carpenter K H, Wilcken B, Kuchel P W, Alexander I E. AAV2/8-mediated correction of OTC deficiency is robust in adult but not neonatal Spf(ash) mice. Mol Ther. 2009 August; 17(8):1340-6.

Ding W, Zhang L, Yan Z, Engelhardt J F. Intracellular trafficking of adeno-associated viral vectors. Gene Therapy 2005, 12: 873-880.

Dominguez E, Marais T, Chatauret N, Benkhelifa-Ziyyat S, Duque S, Ravassard P, Carcenac R, Astord S, de Moura A P, Voit T, Barkats M. Intravenous scAAV9 delivery of a codon-optimized SMN1 sequence rescues SMA mice. Hum Mol Genet. 2011 Feb. 15; 20(4):681-93.

Doenecke A, Krömer A, Scherer M N, Schlitt H J, Geissler E K. AAV plasmid DNA simplifies liver-directed in vivo gene therapy: comparison of expression levels after plasmid DNA-, adeno-associated virus- and adenovirus-mediated liver transfection. J Gene Med. 2010 October; 12(10):810-7.

Dong J Y, Fan P D, Frizzell R A Quantitative analysis of the packaging capacity of recombinant adeno-associated virus. Hum Gene Ther. 1996; 7(17):2102-12.

Duque S, Joussemet B, Riviere C, Marais T, Dubreil L, Douar A M, Fyfe J, Moullier P, Colle M A, Barkats M. Intravenous administration of self-complementary AAV9 enables transgene delivery to adult motor neurons. Mol Ther. 2009 July; 17(7):1187-96.

Eggenhofer E, Doenecke A, Renner P, Slowik P, Piso P, Geissler E K, Schlitt H J, Dahlke M H, Popp F C. High volume naked DNA tail-vein injection restores liver function in Fah-knock out mice. J Gastroenterol Hepatol. 2010 May; 25(5):1002-8.

Fougerousse F, Bartoli M, Poupiot J, Arandel L, Durand M, Guerchet N, Gicquel E, Danos O, Richard I. Phenotypic correction of alpha-sarcoglycan deficiency by intra-arterial injection of a muscle-specific serotype 1 rAAV vector. Mol Ther. 2007 January; 15(1):53-61.

Foust K D, Nurre E, Montgomery C L, Hernandez A, Chan C M, Kaspar B K. Intravascular AAV9 preferentially targets neonatal neurons and adult astrocytes. Nat Biotechnol. 2009 January; 27(1):59-65.

Frauli M, Ribault S, Neuville P, Augé F, Calenda V. Adenoviral-mediated skeletal muscle transcriptional targeting using chimeric tissue-specific promoters. Med Sci Monit. 2003 February; 9(2):BR78-84.

Gonin P, Gaillard C. Gene transfer vector biodistribution: pivotal safety studies in clinical gene therapy development. Gene Therapy. 2004; 11: S98-108.

Goyenvalle A, Vulin A, Fougerousse F, Leturcq F, Kaplan J C, Garcia L, Danos O. Rescue of dystrophic muscle through U7 snRNA-mediated exon skipping. Science. 2004 Dec. 3; 306(5702):1796-9.

Grimm D, et al. Novel Tools for Production and Purification of Recombinant Adenoassociated Virus Vectors. Human Gene Therapy. 1998; 9:2745-2760.

Gruber C, Gratz I K, Murauer E M, Mayr E, Koller U, Bruckner-Tuderman L, Meneguzzi G, Hintner H, Bauer J W. Spliceosome-mediated RNA trans-splicing facilitates targeted delivery of suicide genes to cancer cells. Mol Cancer Ther. 2011 February; 10(2):233-41.

Hacker and Wurn. ENCYCLOPEDIA OF LIFE SCIENCES, 2007

Haire S E, Pang J, Boye S L, Sokal I, Craft C M, Palczewski K, Hauswirth W W, Semple-Rowland S L. Light-driven cone arrestin translocation in cones of postnatal guanylate cyclase-1 knockout mouse retina treated with AAV-GC1. Invest Ophthalmol Vis Sci. 2006 September; 47(9):3745-53.

Himeda C L, Chen X, Hauschka S D. Design and testing of regulatory cassettes for optimal activity in skeletal and cardiac muscles. Methods Mol Biol. 2011; 709:3-19.

Hong G, Ward P, Berns K I. In vitro replication of adeno-associated virus DNA. PNAS. 1992 May 15; 89(10): 4673-7.

Hong G, Ward P, Berns K I. Intermediates of adeno-associated virus DNA replication in vitro. J Virol. 1994 March; 68(3):2011-5.

Ill C R, Yang C Q, Bidlingmaier S M, Gonzales J N, Burns D S, Bartholomew R M, Scuderi P. Optimization of the human factor VIII complementary DNA expression plasmid for gene therapy of hemophilia A Blood Coagul Fibrinolysis. 1997 December; 8 Suppl 2:S23-30.

Jimenez V, Ayuso E, Mallol C, Agudo J, Casellas A, Obach M, Muñoz S, Salavert A, Bosch F. In vivo genetic engineering of murine pancreatic beta cells mediated by single-stranded adeno-associated viral vectors of serotypes 6, 8 and 9. Diabetologia. 2011 Feb. 11. Epub ahead of print.

Kapadia F N and Jha A N. Simultaneous lumbar and intraventricular manometry to evaluate the role and safety of lumbar puncture in raised intracranial pressure following subarchnoid haemorrhage. Br J Neurosurg. 1996 December; 1(6):585-7.

Khani S C, Pawlyk B S, Bulgakov O V, Kasperek E, Young J E, Adamian M, Sun X, Smith A J, Ali R R, Li T. AAV-mediated expression targeting of rod and cone photoreceptors with a human rhodopsin kinase promoter. Invest Ophthalmol Vis Sci. 2007 September; 48(9):3954-61

Koppanati B M, Li J, Reay D P, Wang B, Daood M, Zheng H, Xiao X, Watchko J F, Clemens P R. Improvement of the mdx mouse dystrophic phenotype by systemic in utero AAV8 delivery of a minidystrophin gene. Gene Ther. 2010 Jun. 10.

Lai Y, Yue Y, Duan D. Evidence for the failure of adeno-associated virus serotype 5 to package a viral genome > or =8.2 kb. Mol Ther. 2010 January; 18(1):75-9.

Léveillard T, Sahel J A. Rod-derived cone viability factor for treating blinding diseases: from clinic to redox signaling Sci Transl Med. 2010 Apr. 7; 2(26):26ps16.

Lhériteau E, Libeau L, Stieger K, Deschamps J Y, Mendes-Madeira A, Provost N, Lemoine F, Mellersh C, Ellinwood N M, Cherel Y, Moullier P, Rolling F. The RPGRIP1-deficient dog, a promising canine model for gene therapy. Mol Vis. 2009; 15:349-61.

Lhériteau E, Libeau L, Mendes-Madeira A, Deschamps J Y, Weber M, Le Meur G, Provost N, Guihal C, Moullier P, Rolling F. Regulation of retinal function but nonrescue of vision in RPE65-deficient dogs treated with doxycycline-regulatable AAV vectors. Mol Ther. 2010 June; 18(6): 1085-93.

Li M, Jayandharan G R, Li B, Ling C, Ma W, Srivastava A, Zhong L. High-Efficiency Transduction of Fibroblasts and Mesenchymal Stem Cells by Tyrosine-Mutant AAV2 Vectors for Their Potential Use in Cellular Therapy. Hum Gene Ther. 2010 May 27.

Li Z, Marchand P, Humbert J, Babinet C, Paulin D. Desmin sequence elements regulating skeletal muscle-specific expression in transgenic mice. Development. 1993 March; 117(3):947-59.

Lorain S, Gross D A, Goyenvalle A, Danos O, Davoust J, Garcia L. Transient immunomodulation allows repeated injections of AAV1 and correction of muscular dystrophy in multiple muscles. Mol Ther. 2008 March; 16(3):541-7.

Lostal, W. et al, Human Mol. Gen., 2010, 19(10):1897-1907.

Lowery R L, Majewska A K. Intracranial injection of adeno-associated viral vectors. J Vis Exp. 2010 November 17; (45):pii 2140.

McCarty D M. Self-complementary AAV vectors; advances and applications. Mol Ther. 2008 October; 16(10):1648-56. Epub 2008 Aug. 5.

Millington-Ward S, Chadderton N, O'Reilly M, Palfi A, Goldmann T, Kilty C, Humphries M, Wolfrum U, Bennett J, Humphries P, Kenna P F, Farrar G. Suppression and Replacement Gene Therapy for Autosomal Dominant Disease in a Murine Model of Dominant Retinitis Pigmentosa. Mol Ther. 2011 Jan. 11

Miyazaki J, Takaki S, Araki K, Tashiro F, Tominaga A, Takatsu K, Yamamura K. Expression vector system based on the chicken beta-actin promoter directs efficient production of interleukin-5 Gene. 1989; 79:269-77.

Nash K, Chen W, McDonald W F, Zhou X, Muzyczka N. Complete in vitro reconstitution of adeno-associated virus DNA replication requires the minichromosome maintenance complex proteins. J Virol. 2007 June; 81(11):5777-87.

Ni T H, Zhou X, McCarty D M, Zolotukhin I, Muzyczka N. In vitro replication of adeno-associated virus DNA. J Virol. 1994 February; 68(2):1128-38.

Pang J J, Boye S L, Kumar A, Dinculescu A, Deng W, Li J, Li Q, Rani A, Foster T C, Chang B, Hawes N L, Boatright J H, Hauswirth W W. AAV-mediated gene therapy for retinal degeneration in the rd10 mouse containing a recessive PDEbeta mutation. Invest Ophthalmol Vis Sci. 2008 October; 49(10):4278-83. Epub 2008 Jun. 27.

Pang J J, Dai X, Boye S E, Barone I, Boye S L, Mao S, Everhart D, Dinculescu A, Liu L, Umino Y, Lei B, Chang B, Barlow R, Strettoi E, Hauswirth W W. Long-term Retinal Function and Structure Rescue Using Capsid Mutant AAV8 Vector in the rd10 Mouse, a Model of Recessive Retinitis Pigmentosa. Mol Ther. 2011 February; 19(2):234-42.

Philip R, Brunette E, Kilinski L, Murugesh D, McNally M A, Ucar K, Rosenblatt J, Okarma T B, Lebkowski J S. Efficient and sustained gene expression in primary T lymphocytes and primary and cultured tumor cells mediated by adeno-associated virus plasmid DNA complexed to cationic liposomes. Mol Cell Biol. 1994 April; 14(4): 2411-8.

Piétri-Rouxel F, Gentil C, Vassilopoulos S, Baas D, Mouisel E, Ferry A, Vignaud A, Hourdé C, Marty I, Schaeffer L, Voit T, Garcia L. EMBO J. 2010 February; 29(3):643-54.

Rolling F. *AAV-mediated gene therapy for the treatment of retinal diseases*. Curr Gene Ther. 2010 Oct. 1; 10(5):318.

Romero N B, Braun S, Benveniste O, Leturcq F, Hogrel J Y, Morris G E, Barois A, Eymard B, Payan C, Ortega V, Boch A L, Lejean L, Thioudellet C, Mourot B, Escot C, Choquel A, Recan D, Kaplan J C, Dickson G, Klatzmann D, Molinier-Frenckel V, Guillet J G, Squiban P, Herson S, Fardeau M. Phase I study of dystrophin plasmid-based gene therapy in Duchenne/Becker muscular dystrophy. Hum Gene Ther. 2004 November; 15(11): 1065-76.

Silva G, Poirot L, Galetto R, Smith J, Montoya G, Duchateau P, Pâques F. Meganucleases and other Tools for Targeted Genome Engineering: Perspectives and Challenges for Gene Therapy. Curr Gene Ther. 2011 Feb. 1; 11(1):11-27.

Snyder-Keller A, McLear J A, Hathorn T, Messer A Early or late-stage anti-N-terminal Huntingtin intrabody gene therapy reduces pathological features in B6.HDR6/1 mice. J Neuropathol Exp Neurol. 2010 October; 69(10): 1078-85.

Stieger K, Chauveau C, Rolling F. Preclinical studies on specific gene therapy for recessive retinal degenerative diseases. Curr Gene Ther. 2010 Oct. 1; 10(5):389-403.

Stieger K, Lorenz B. Gene therapy for vision loss—recent developments. Discov Med. 2010 November; 10(54):425-33.

Sun N, Liang J, Abil Z, Zhao H. Optimized TAL effector nucleases (TALENs) for use in treatment of sickle cell disease. Mol Biosyst. 2012 Apr. 1; 8(4):1255-63.

Timmers A M, Zhang H, Squitieri A, Gonzalez-Pola C. Subretinal injections in rodent eyes: effects on electrophysiology and histology of rat retina Mol Vis. 2001 Jun. 22; 7:131-7.

Toromanoff A, Adjali O, Larcher T, Hill M, Guigand L, Chenuaud P, Deschamps J Y, Gauthier O, Blancho G, Vanhove B, Rolling F, Cherel Y, Moullier P, Anegon I, Le Guiner C. Lack of immunotoxicity after regional intravenous (RI) delivery of rAAV to nonhuman primate skeletal muscle. Mol Ther. 2010 January; 18(1):151-60.

Urabe, M., Ding, C., and Kotin, R. M. (2002). Insect cells as a factory to produce adeno-associated virus type 2 vectors. Hum Gene Ther 13, 1935-43.

van der Marel S, Comijn E M, Verspaget H W, van Deventer S, van den Brink G R, Petry H, Hommes D W, Ferreira V. Neutralizing antibodies against adeno-associated viruses in inflammatory bowel disease patients: Implications for gene therapy. Inflamm Bowel Dis. 2011 Mar. 2. Epub ahead of print.

Varenika V, Kells A P, Valles F, Hadaczek P, Forsayeth J, Bankiewicz K S. Controlled dissemination of AAV vectors in the primate brain. Prog Brain Res. 2009; 175:163-72.

Virag T, Cecchini S, Kotin R M. Producing recombinant adeno-associated virus in foster cells: overcoming production limitations using a baculovirus-insect cell expression strategy. Hum Gene Ther. 2009 August; 20(8):807-17.

Wang B, Li J, Fu F H, Xiao X. Systemic human minidystrophin gene transfer improves functions and life span of dystrophin and dystrophin/utrophin-deficient mice. J Orthop Res. 2009 April; 27(4):421-6.

Wang S, Liu P, Song L, Lu L, Zhang W, Wu Y. Adeno-associated virus (AAV) based gene therapy for eye diseases. Cell Tissue Bank 2011 Feb. 23. Epub ahead of print.

Ward P, Berns K I. In vitro rescue of an integrated hybrid adeno-associated virus/simian virus 40 genome. J Mol Biol. 1991 Apr. 20: 218(4): 791-804.

Weber M, Rabinowitz J, Provost N, Conrath H, Folliot S, Briot D, Chérel Y, Chenuaud P, Samulski J, Moullier P, Rolling F. Recombinant adeno-associated virus serotype 4 mediates unique and exclusive long-term transduction of retinal pigmented epithelium in rat, dog, and nonhuman primate after subretinal delivery. Mol Ther. 2003 June; 7(6):774-81.

White J D, Thesier D M, Swain J B, Katz M G, Tomasulo C, Henderson A, Wang L, Yarnall C, Fargnoli A, Sumaroka M, Isidro A, Petrov M, Holt D, Nolen-Walston R, Koch W J, Stedman H H, Rabinowitz J, Bridges C R. Myocardial gene delivery using molecular cardiac surgery with recombinant adeno-associated virus vectors in vivo. Gene Ther. 2011 Jan. 13. Epub ahead of print.

Wu T, Töpfer K, Lin S W, Li H, Bian A, Zhou X Y, High K A, Ertl H C. Self-complementary AAVs Induce More Potent Transgene Product-specific Immune Responses Compared to a Single-stranded Genome. Mol Ther. 2012 March; 20(3):572-9.

The invention claimed is:

1. An isolated linear capsid-free nucleic acid molecule comprising in this order: a first adeno-associated virus (AAV) inverted terminal repeat (ITR), a nucleotide sequence of interest and a second AAV ITR, wherein said nucleic acid molecule is devoid of AAV capsid protein coding sequences.

2. The isolated linear capsid-free nucleic acid molecule of claim 1, wherein the nucleotide sequence of interest is an expression cassette of an exogenous DNA.

3. The isolated linear capsid-free nucleic acid molecule of claim 1, wherein said nucleic acid molecule is single-stranded.

4. The isolated linear capsid-free nucleic acid molecule of claim 1, which is devoid of AAV rep protein coding sequences.

5. The isolated linear capsid-free nucleic acid molecule of claim 1, wherein the nucleotide sequence of interest comprises from about 4,200 to about 15,000 nucleotides.

6. The isolated linear capsid-free nucleic acid molecule of claim 2, wherein the exogenous DNA sequence encodes a protein or a sense or anti-sense oligonucleotide.

7. The isolated linear capsid-free nucleic acid molecule of claim 2, comprising a promoter directing the expression of said exogenous DNA preferentially or exclusively in a tissue- or organ-specific manner.

8. The isolated linear capsid-free nucleic acid molecule of claim 2, wherein the exogenous DNA encodes U7 snRNA, RNAi or siRNA.

9. A method of producing an isolated linear capsid-free nucleic acid molecule according to claim 1, said method comprising:
   (a) providing cells comprising a nucleic acid sequence comprising two AAV ITRs and a nucleotide sequence of interest positioned between the ITRs; wherein the nucleic acid sequence is devoid of AAV capsid protein encoding genes and the cells do not express AAV capsid proteins;
   (b) optionally providing into the cell AAV Rep genes or proteins, if not already present in the cells, but not AAV Cap genes or proteins;
   (c) growing the cells under conditions permitting replication and release of DNA comprising the ITRs and the expression cassette and constituting AAV0 vector;
   (d) collecting rescued AAV0 vector from the cells.

10. The method of claim 9, wherein the cells are Sf9.

11. A method for mediating the expression of exogenous DNA in a mammalian cell comprising the steps of:
   (a) delivering to the cell an effective amount of an isolated linear capsid-free nucleic acid molecule according to claim 1;
   (b) growing the cell under conditions permitting the expression by the cell of the exogenous DNA;
wherein the effective amount is sufficient to permit a desired level of expression by the cell of the exogenous DNA.

12. The method of claim 11, wherein the delivering comprises simply introducing the isolated linear capsid-free nucleic acid molecule in the extracellular medium and does not comprise use of any other transduction means.

13. A method for effecting the expression of a desired gene product or oligonucleotide in a cell comprising contacting at least one isolated linear capsid-free nucleic acid molecule according to claim 1 with the cell's surface in the absence of a transfection agent or additional physical means to facilitate entry of said at least one isolated linear capsid-free nucleic acid molecule into the cell.

14. A method for delivering a nucleotide sequence of interest mediating the expression of exogenous DNA in a cell, an organ or tissue of a subject, comprising administering to said subject an isolated linear capsid-free nucleic acid molecule of comprising in this order: a first adeno-associated virus (AAV) inverted terminal repeat (ITR), a nucleotide sequence of interest and a second AAV ITR, wherein said nucleic acid molecule is devoid of AAV capsid protein coding sequences.

15. A method for mediating the expression of an exogenous DNA in a cell, an organ or tissue of a subject, comprising administering to said subject an isolated linear capsid-free nucleic acid molecule comprising in this order: a first adeno-associated virus (AAV) inverted terminal repeat (ITR), a nucleotide sequence of interest and a second AAV ITR, wherein said nucleic acid molecule is devoid of AAV capsid protein coding sequences.

16. The method according to claim 14, wherein the delivering step comprises systemic delivery to said mammal, via intra-arterial or intramuscular injection.

17. The method according to claim 11, wherein the delivering step takes place in the absence of a transfection agent or additional physical means to facilitate entry of said at least one isolated linear capsid-free nucleic acid molecule into the cell.

* * * * *

SEQUENCE LISTING

<160> NUMBER OF SEQ ID NOS: 14

<210> SEQ ID NO 1
<211> LENGTH: 145
<212> TYPE: DNA
<213> ORGANISM: adeno-associated virus 2

<400> SEQUENCE: 1

```
ttggccactc cctctctgcg cgctcgctcg ctcactgagg ccgggcgacc aaaggtcgcc      60
cgacgcccgg gctttgcccg ggcggcctca gtgagcgagc gagcgcgcag agagggagtg     120
gccaactcca tcactagggg ttcct                                           145
```

<210> SEQ ID NO 2
<211> LENGTH: 144
<212> TYPE: DNA
<213> ORGANISM: adeno-associated virus 2

<400> SEQUENCE: 2

```
ggaacccta gtgatggagt tggccactcc ctctctgcgc gctcgctcgc tcactgaggc      60
cgggcgacca aaggtcgccc gacgcccggg cttgcccgg gcggcctcag tgagcgagcg     120
agcgcgcaga gagggagtgg ccaa                                            144
```

<210> SEQ ID NO 3
<211> LENGTH: 4718
<212> TYPE: DNA
<213> ORGANISM: adeno-associated virus 1

<400> SEQUENCE: 3

```
ttgcccactc cctctctgcg cgctcgctcg ctcggtgggg cctgcggacc aaaggtccgc      60
agacggcaga gctctgctct gccggcccca ccgagcgagc gagcgcgcag agagggagtg     120
ggcaactcca tcactagggg taatcgcgaa gcgcctccca cgctgccgcg tcagcgctga    180
cgtaaattac gtcataggggg agtggtcctg tattagctgt cacgtgagtg cttttgcgac    240
attttgcgac accacgtggc catttagggt atatatggcc gagtgagcga gcaggatctc    300
cattttgacc gcgaaatttg aacgagcagc agccatgccg ggcttctacg agatcgtgat    360
caaggtgccg agcgacctgg acgagcacct gccgggcatt tctgactcgt ttgtgagctg    420
ggtggccgag aaggaatggg agctgccccc ggattctgac atggatctga atctgattga    480
gcaggcaccc ctgaccgtgg ccgagaagct gcagcgcgac ttcctggtcc aatggcgccg    540
cgtgagtaag gccccggagg ccctcttctt tgttcagttc gagaagggcg agtcctactt    600
ccacctccat attctggtgg agaccacggg ggtcaaatcc atggtgctgg ccgcttcct    660 gagtcagatt agggacaagc tggtgcagac catctaccgc gggatcgagc cgaccctgcc    720
caactggttc gcggtgacca agacgcgtaa tggcgccgga gggggaaaca aggtggtgga    780
cgagtgctac atccccaact acctcctgcc caagactcag ccgagctgc agtgggcgtg    840 gactaacatg gaggagtata taagcgcctg tttgaacctg gccgagcgca acggctcgt    900 ggcgcagcac ctgacccacg tcagccagac ccaggagcag aacaaggaga atctgaaccc   960
caattctgac gcgcctgtca tccggtcaaa aacctccgcg cgctacatgg agctggtcgg    1020
gtggctggtg gaccggggca tcacctccga gaagcagtgg atccaggagg accaggcctc    1080
gtacatctcc ttcaacgccg cttccaactc gcggtcccag atcaaggccg ctctggacaa    1140
tgccggcaag atcatggcgc tgaccaaatc cgcgcccgac tacctggtag ccccgctcc    1200 gcccgcggac attaaaaacca accgcatcta ccgcatcctg gagctgaacg gctacgaacc    1260
```

```
tgcctacgcc ggctccgtct ttctcggctg ggcccagaaa aggttcggga agcgcaacac    1320
catctggctg tttgggccgg ccaccacggg caagaccaac atcgcggaag ccatcgccca    1380
cgccgtgccc ttctacggct gcgtcaactg gaccaatgag aactttccct tcaatgattg    1440
cgtcgacaag atggtgatct ggtgggagga gggcaagatg acggccaagg tcgtggagtc    1500
cgccaaggcc attctcggcg gcagcaaggt gcgcgtggac caaaagtgca agtcgtccgc    1560
ccagatcgac cccaccccg tgatcgtcac ctccaacacc aacatgtgcg ccgtgattga    1620
cgggaacagc accaccttcg agcaccagca gccgttgcag gaccggatgt tcaaatttga    1680
actcacccgc cgtctggagc atgactttgg caaggtgaca aagcaggaag tcaaagagtt    1740
cttccgctgg gcgcaggatc acgtgaccga ggtggcgcat gagttctacg tcagaaaggg    1800
tggagccaac aaaagacccg ccccgatga cgcggataaa agcgagccca gcgggcctg     1860 cccctcagtc gcggatccat cgacgtcaga cgcggaagga gctccggtgg actttgccga    1920
caggtaccaa aacaaatgtt ctcgtcacgc gggcatgctt cagatgctgt ttccctgcaa    1980
gacatgcgag agaatgaatc agaatttcaa catttgcttc acgcacggga cgagagactg    2040
ttcagagtgc ttccccggcg tgtcagaatc tcaaccggtc gtcagaaaga ggacgtatcg    2100
gaaactctgt gccattcatc atctgctggg gcgggctccc gagattgctt gctcggcctg    2160
cgatctggtc aacgtggacc tggatgactg tgtttctgag caataaatga cttaaaccag    2220
gtatggctgc cgatggttat cttccagatt ggctcgagga caacctctct gagggcattc    2280
gcgagtggtg ggacttgaaa cctggagccc cgaagcccaa agccaaccag caaaagcagg    2340
acgacggccg gggtctggtg cttcctggct acaagtacct cggacccttc aacggactcg    2400
acaaggggga gcccgtcaac gcggcggacg cagcggccct cgagcacgac aaggcctacg    2460
accagcagct caaagcgggt gacaatccgt acctgcggta taaccacgcc gacgccgagt    2520
ttcaggagcg tctgcaagaa gatacgtctt ttggggcaa cctcgggcga gcagtcttcc    2580
aggccaagaa gcgggttctc gaacctctcg gtctggttga ggaaggcgct aagacggctc    2640
ctggaaagaa acgtccggta gagcagtcgc acaagagcc agactcctcc tcgggcatcg    2700
gcaagacagg ccagcagccc gctaaaaaga gactcaattt tggtcagact ggcgactcag    2760
agtcagtccc cgatccacaa cctctcggag aacctccagc aaccccgct gctgtgggac    2820 ctactacaat ggcttcaggc ggtggcgcac caatggcaga caataacgaa ggcgccgacg    2880
gagtgggtaa tgcctcagga aattggcatt gcgattccac atggctgggc gacagagtca    2940
tcaccaccag caccgcacc tgggccttgc ccacctacaa taaccacctc tacaagcaaa    3000
tctccagtgc ttcaacgggg gccagcaacg acaaccacta cttcggctac agcaccccct    3060
gggggtattt tgatttcaac agattccact gccacttttc accacgtgac tggcagcgac    3120
tcatcaacaa caattgggga ttccggccca agagactcaa cttcaaactc ttcaacatcc    3180
aagtcaagga ggtcacgacg aatgatggcg tcacaaccat cgctaataac cttaccagca    3240
cggttcaagt cttctcggac tcggagtacc agcttccgta cgtcctcggc tctgcgcacc    3300
agggctgcct ccctcgttc ccggcggacg tgttcatgat ccgcaatac ggctacctga    3360 cgctcaacaa tggcagccaa gccgtgggac gttcatcctt ttactgcctg gaatatttcc    3420
cttctcagat gctgagaacg ggcaacaact ttaccttcag ctacacctt gaggaagtgc    3480 cttttccacag cagctacgcg cacagccaga gcctggaccg gctgatgaat cctctcatcg    3540
accaatacct gtattacctg aacagaactc aaaatcagtc cggaagtgcc caaaacaagg    3600
```

```
acttgctgtt tagccgtggg tctccagctg gcatgtctgt tcagcccaaa aactggctac    3660
ctggaccctg ttatcggcag cagcgcgttt ctaaaacaaa aacagacaac aacaacagca    3720
attttacctg gactggtgct tcaaaatata acctcaatgg gcgtgaatcc atcatcaacc    3780
ctggcactgc tatggcctca cacaaagacg acgaagacaa gttctttccc atgagcggtg    3840
tcatgatttt tggaaaagag agcgccggag cttcaaacac tgcattggac aatgtcatga    3900
ttacagacga agaggaaatt aaagccacta ccctgtggc caccgaaaga tttgggaccg    3960
tggcagtcaa tttccagagc agcagcacag accctgcgac cggagatgtg catgctatgg    4020
gagcattacc tggcatggtg tggcaagata gagacgtgta cctgcagggt cccatttggg    4080
ccaaaattcc tcacacagat ggacactttc acccgtctcc tcttatgggc ggctttggac    4140
tcaagaaccc gcctcctcag atcctcatca aaaacacgcc tgttcctgcg aatcctccgg    4200
cggagttttc agctacaaag tttgcttcat tcatcaccca atactccaca ggacaagtga    4260
gtgtggaaat tgaatgggag ctgcagaaag aaaacagcaa gcgctggaat cccgaagtgc    4320
agtacacatc caattatgca aaatctgcca acgttgattt tactgtggac aacaatggac    4380
tttatactga gcctcgcccc attggcaccc gttaccttac ccgtcccctg taattacgtg    4440
ttaatcaata accggttga ttcgtttcag ttgaactttg gtctcctgtc cttcttatct     4500
tatcggttac catggttata gcttacacat taactgcttg gttgcgcttc gcgataaaag    4560
acttacgtca tcgggttacc cctagtgatg gagttgccca ctccctctct gcgcgctcgc    4620
tcgctcggtg gggcctgcgg accaaaggtc cgcagacggc agagctctgc tctgccggcc    4680
ccaccgagcg agcgagcgcg cagagaggga gtgggcaa                            4718

<210> SEQ ID NO 4
<211> LENGTH: 4726
<212> TYPE: DNA
<213> ORGANISM: adeno-associated virus 3

<400> SEQUENCE: 4
ttggccactc cctctatgcg cactcgctcg ctcggtgggg cctggcgacc aaaggtcgcc      60
agacggacgt gctttgcacg tccggcccca ccgagcgagc gagtgcgcat agagggagtg     120
gccaactcca tcactagagg tatggcagtg acgtaacgcg aagcgcgcga agcgagacca     180
cgcctaccag ctgcgtcagc agtcaggtga ccctttttgcg acagtttgcg acaccacgtg     240
gccgctgagg gtatatattc tcgagtgagc gaaccaggag ctccattttg accgcgaaat     300 tgaacgagc agcagccatg ccggggttct acgagattgt cctgaaggtc ccgagtgacc     360
tggacgagcg cctgccgggc atttctaact cgtttgttaa ctgggtggcc gagaaggaat     420
gggacgtgcc gccggattct gacatggatc cgaatctgat tgagcaggca ccctgaccg     480 tggccgaaaa gcttcagcgc gagttcctgg tggagtggcg ccgcgtgagt aaggcccgg     540 aggccctctt ttttgtccag ttcgaaaagg gggagaccta cttccacctg cacgtgctga    600
ttgagaccat cggggtcaaa tccatggtgg tcggccgcta cgtgagccag attaaagaga    660
agctggtgac ccgcatctac cgcggggtcg agccgcagct tccgaactgg ttcgcggtga    720
ccaaaacgcg aaatggcgcc ggggggcgga caaggtggt ggacgactgc tacatcccca    780
actacctgct ccccaagacc cagcccgagc tccagtgggc gtggactaac atggaccagt    840
atttaagcgc ctgtttgaat ctcgcggagc gtaaacggct ggtggcgcag catctgacgc    900
acgtgtcgca gacgcaggag cagaacaaag agaatcagaa ccccaattct gacgcgccgg    960
tcatcaggtc aaaaaacctca gccaggtaca tggagctggt cgggtggctg gtggaccgcg   1020
```

```
ggatcacgtc agaaaagcaa tggattcagg aggaccaggc ctcgtacatc tccttcaacg    1080
ccgcctccaa ctcgcggtcc cagatcaagg ccgcgctgga caatgcctcc aagatcatga    1140
gcctgacaaa gacggctccg gactacctgg tgggcagcaa cccgccggag gacattacca    1200
aaaatcggat ctaccaaatc ctggagctga acgggtacga tccgcagtac gcggcctccg    1260
tcttcctggg ctgggcgcaa aagaagttcg ggaagaggaa caccatctgg ctctttgggc    1320
cggccacgac gggtaaaacc aacatcgcgg aagccatcgc ccacgccgtg cccttctacg    1380
gctgcgtaaa ctggaccaat gagaactttc ccttcaacga ttgcgtcgac aagatggtga    1440
tctggtggga ggagggcaag atgacggcca aggtcgtgga gagcgccaag gccattctgg    1500
gcggaagcaa ggtgcgcgtg gaccaaaagt gcaagtcatc ggcccagatc gaacccactc    1560
ccgtgatcgt cacctccaac accaacatgt gcgccgtgat tgacgggaac agcaccacct    1620
tcgagcatca gcagccgctg caggaccgga tgtttgaatt tgaacttacc cgccgtttgg    1680
accatgactt tgggaaggtc accaaacagg aagtaaagga cttttttccgg tgggcttccg    1740 atcacgtgac tgacgtggct catgagttct acgtcagaaa gggtggagct aagaaacgcc    1800
ccgcctccaa tgacgcggat gtaagcgagc caaaacggga gtgcacgtca cttgcgcagc    1860
cgacaacgtc agacgcggaa gcaccggcgg actacgcgga caggtaccaa aacaaatgtt    1920
ctcgtcacgt gggcatgaat ctgatgcttt ttccctgtaa acatgcgag agaatgaatc    1980 aaatttccaa tgtctgtttt acgcatggtc aaagagactg tggggaatgc ttccctggaa    2040
tgtcagaatc tcaacccgtt tctgtcgtca aaagaagac ttatcagaaa ctgtgtccaa     2100
ttcatcatat cctgggaagg gcacccgaga ttgcctgttc ggcctgcgat ttggccaatg    2160
tggacttgga tgactgtgtt tctgagcaat aaatgactta aaccaggtat ggctgctgac    2220
ggttatcttc cagattggct cgaggacaac ctttctgaag gcattcgtga gtggtgggct    2280
ctgaaacctg gagtccctca acccaaagcg aaccaacaac accaggacaa ccgtcggggt    2340
cttgtgcttc cgggttacaa atacctcgga cccggtaacg gactcgacaa aggagagccg    2400
gtcaacgagg cggacgcggc agccctcgaa cacgacaaag cttacgacca gcagctcaag    2460
gccggtgaca acccgtacct caagtacaac cacgccgacc ccgagtttca ggagcgtctt    2520
caagaagata cgtctttggg gggcaacctt ggcagagcag tcttccaggc caaaaagagg    2580
atccttgagc ctcttggtct ggttgaggaa gcagctaaaa cggctcctgg aaagaagggg    2640
gctgtagatc agtctcctca ggaaccggac tcatcatctg gtgttggcaa atcgggcaaa    2700
cagcctgcca gaaaaagact aaatttcggt cagactggag actcagagtc agtcccagac    2760
cctcaacctc tcggagaacc accagcagcc cccacaagtt tgggatctaa tacaatggct    2820
tcaggcggtg gcgcaccaat ggcagacaat aacgagggtg ccgatggagt gggtaattcc    2880
tcaggaaatt ggcattgcga ttcccaatgg ctgggcgaca gagtcatcac caccagcacc    2940
agaacctggg ccctgcccac ttacaacaac catctctaca gcaaatctc cagccaatca    3000 ggagcttcaa acgacaacca ctactttggc tacagcaccc cttgggggta ttttgacttt    3060
aacagattcc actgccactt ctcaccacgt gactggcagc gactcattaa caacaactgg    3120
ggattccggc caagaaaact cagcttcaag ctcttcaaca tccaagttag aggggtcacg    3180
cagaacgatg gcacgacgac tattgccaat aaccttacca gcacggttca agtgtttacg    3240
gactcggagt atcagctccc gtacgtgctc gggtcggcgc accaaggctg tctcccgccg    3300
tttccagcgg acgtcttcat ggtccctcag tatggatacc tcaccctgaa caacggaagt    3360
```

```
caagcggtgg gacgctcatc cttttactgc ctggagtact tcccttcgca gatgctaagg      3420
actggaaata acttccaatt cagctatacc ttcgaggatg tacctttca cagcagctac       3480 gctcacagcc agagtttgga tcgcttgatg aatcctctta ttgatcagta tctgtactac      3540
ctgaacagaa cgcaaggaac aacctctgga acaaccaacc aatcacggct gcttttagc       3600 caggctgggc ctcagtctat gtctttgcag gccagaaatt ggctacctgg ccctgctac       3660 cggcaacaga gactttcaaa gactgctaac gacaacaaca acagtaactt ccttggaca       3720 gcggccagca aatatcatct caatggccgc gactcgctgg tgaatccagg accagctatg      3780
gccagtcaca aggacgatga agaaaaattt ttccctatgc acggcaatct aatatttggc      3840
aaagaaggga caacggcaag taacgcagaa ttagataatg taatgattac ggatgaagaa      3900
gagattcgta ccaccaatcc tgtggcaaca gagcagtatg gaactgtggc aaataacttg      3960
cagagctcaa atacagctcc cacgactgga actgtcaatc atcagggggc cttacctggc      4020
atggtgtggc aagatcgtga cgtgtaccct caaggaccta tctggcaaa gattcctcac      4080 acggatggac actttcatcc ttctcctctg atgggaggct ttggactgaa acatcecgcct    4140 cctcaaatca tgatcaaaaa tactccggta ccggcaaatc ctccgacgac tttcagcccg      4200
gccaagtttg cttcatttat cactcagtac tccactggaa aggtcagcgt ggaaattgag      4260
tgggagctac agaaagaaaa cagcaaacgt tggaatccag agattcagta cacttccaac      4320
tacaacaagt ctgttaatgt ggactttact gtagacacta atggtgttta tagtgaacct      4380
cgccctattg gaacccggta tctcacacga aacttgtgaa tcctggttaa tcaataaacc      4440
gtttaattcg tttcagttga actttggctc ttgtgcactt cttatcttt atcttgtttc       4500 catggctact gcgtagataa gcagcggcct gcggcgcttg cgcttcgcgg tttacaactg      4560
ctggttaata tttaactctc gccataccte tagtgatgga gttggccact ccctctatgc      4620
gcactcgctc gctcggtggg gcctggcgac caaggtcgc cagacggacg tgctttgcac       4680
gtccggcccc accgagcgag cgagtgcgca tagagggagt ggccaa                     4726

<210> SEQ ID NO 5
<211> LENGTH: 4767
<212> TYPE: DNA
<213> ORGANISM: adeno-associated virus 4

<400> SEQUENCE: 5
ttggccactc cctctatgcg cgctcgctca ctcactcggc cctggagacc aaaggtctcc       60
agactgccgg cctctggccg gcagggccga gtgagtgagc gagcgcgcat agagggagtg      120
gccaactcca tcatctaggt ttgcccactg acgtcaatgt gacgtcctag ggttagggag      180
gtccctgtat tagcagtcac gtgagtgtcg tatttcgcgg agcgtagcgg agcgcatacc      240
aagctgccac gtcacagcca cgtggtccgt ttgcgacagt ttgcgacacc atgtggtcag      300
gagggtatat aaccgcgagt gagccagcga ggagctccat tttgcccgcg aatttttgaac     360 gagcagcagc catgccgggg ttctacgaga tcgtgctgaa ggtgcccagc gacctggacg      420
agcacctgcc cggcatttct gactcttttg tgagctgggt ggccgagaag gaatgggagc      480
tgccgccgga ttctgacatg gacttgaatc tgattgagca ggcaccctg accgtggccg       540 aaaagctgca acgcgagttc ctggtcgagt ggcgccgcgt gagtaaggcc ccggaggccc      600
tcttctttgt ccagttcgag aaggggaca gctacttcca cctgcacatc ctggtggaga      660
ccgtgggcgt caaatccatg gtggtgggcc gctacgtgag ccagattaaa gagaagctgg      720
tgacccgcat ctaccgcggg gtcgagccgc agcttccgaa ctggttcgcg gtgaccaaga      780
```

-continued

```
cgcgtaatgg cgccggaggc gggaacaagg tggtggacga ctgctacatc cccaactacc    840
tgctccccaa gacccagccc gagctccagt gggcgtggac taacatggac cagtatataa    900
gcgcctgttt gaatctcgcg gagcgtaaac ggctggtggc gcagcatctg acgcacgtgt    960
cgcagacgca ggagcagaac aaggaaaacc agaaccccaa ttctgacgcg ccggtcatca   1020
ggtcaaaaac ctccgccagg tacatggagc tggtcgggtg ctggtggac cgcgggatca    1080
cgtcagaaaa gcaatggatc caggaggacc aggcgtccta catctccttc aacgccgcct   1140
ccaactcgcg gtcacaaatc aaggccgcgc tggacaatgc ctccaaaatc atgagcctga   1200
caaagacggc tccggactac ctggtgggcc agaacccgcc ggaggacatt ccagcaacc    1260
gcatctaccg aatcctcgag atgaacgggt acgatccgca gtacgcggcc tccgtcttcc   1320
tgggctgggc gcaaaagaag ttcgggaaga ggaacaccat ctggctcttt gggccggcca   1380
cgacgggtaa aaccaacatc gcggaagcca tcgcccacgc cgtgcccttc tacggctgcg   1440
tgaactggac caatgagaac tttccgttca acgattgcgt cgacaagatg gtgatctggt   1500
gggaggaggg caagatgacg gccaaggtcg tagagagcgc caaggccatc ctgggcggaa   1560
gcaaggtgcg cgtggaccaa aagtgcaagt catcggccca gatcgaccca actcccgtga   1620
tcgtcacctc caacaccaac atgtgcgcgg tcatcgacgg aaactcgacc accttcgagc   1680
accaacaacc actccaggac cggatgttca agttcgagct caccaagcgc ctggagcacg   1740
actttggcaa ggtcaccaag caggaagtca agactttttt ccggtgggcg tcagatcacg   1800
tgaccgaggt gactcacgag ttttacgtca gaaagggtgg agctagaaag aggcccgccc   1860
ccaatgacgc agatataagt gagcccaagc gggcctgtcc gtcagttgcg cagccatcga   1920
cgtcagacgc ggaagctccg gtggactacg cggacaggta ccaaaacaaa tgttctcgtc   1980
acgtgggtat gaatctgatg cttttccct gccggcaatg cgagagaatg aatcagaatg    2040
tggacatttg cttcacgcac ggggtcatgg actgtgccga gtgcttcccc gtgtcagaat   2100
ctcaacccgt gtctgtcgtc agaaagcgga cgtatcagaa actgtgtccg attcatcaca   2160
tcatggggag ggcgcccgag gtggcctgct cggcctgcga actggccaat gtggacttgg   2220
atgactgtga catggaacaa taaatgactc aaaccagata tgactgacgg ttaccttcca   2280
gattggctag aggacaacct ctctgaaggc gttcgagagt ggtgggcgct gcaacctgga   2340
gcccctaaac ccaaggcaaa tcaacaacat caggacaacg ctcggggtct tgtgcttccg   2400
ggttacaaat acctcggacc cggcaacgga ctcgacaagg gggaacccgt caacgcagcg   2460
gacgcggcag ccctcgagca cgacaaggcc tacgaccagc agctcaaggc cggtgacaac   2520
ccctacctca gtacaaccca cgccgacgcg gagttccagc agcggcttca gggcgacaca   2580
tcgtttgggg gcaacctcgg cagagcagtc ttccaggcca aaagagggt tcttgaacct    2640
cttggtctgg ttgagcaagc gggtgagacg gctcctggaa agaagagacc gttgattgaa   2700
tcccccagc agcccgactc ctccacgggt atcggcaaaa aggcaagca gccggctaaa    2760
aagaagctcg ttttcgaaga cgaaactgga gcaggcgacg gaccccctga gggatcaact   2820
tccggagcca tgtctgatga cagtgagatg cgtgcagcag ctggcggagc tgcagtcgag   2880
ggcggacaag gtgccgatgg agtgggtaat gcctcgggtg attggcattg cgattccacc   2940
tggtctgagg gccacgtcac gaccaccagc accagaacct gggtcttgcc cacctacaac   3000
aaccacctct acaagcgact cggagagagc ctgcagtcca acacctacaa cggattctcc   3060
accccctggg gatactttga cttcaaccgc ttccactgcc acttctcacc acgtgactgg   3120
```

```
cagcgactca tcaacaacaa ctggggcatg cgacccaaag ccatgcgggt caaaatcttc    3180
aacatccagg tcaaggaggt cacgacgtcg aacggcgaga caacggtggc taataacctt    3240
accagcacgg ttcagatctt tgcggactcg tcgtacgaac tgccgtacgt gatggatgcg    3300
ggtcaagagg gcagcctgcc tccttttccc aacgacgtct ttatggtgcc ccagtacggc    3360
tactgtggac tggtgaccgg caacacttcg cagcaacaga ctgacagaaa tgccttctac    3420
tgcctggagt actttccttc gcagatgctg cggactggca caactttga aattacgtac     3480 agttttgaga aggtgccttt ccactcgatg tacgcgcaca gccagagcct ggaccggctg    3540
atgaaccctc tcatcgacca gtacctgtgg ggactgcaat cgaccaccac cggaaccacc    3600
ctgaatgccg ggactgccac caccaacttt accaagctgc ggcctaccaa cttttccaac    3660
tttaaaaaga ctggctgccc cgggccttca atcaagcagc agggcttctc aaagactgcc    3720
aatcaaaact acaagatccc tgccaccggg tcagacagtc tcatcaaata cgagacgcac    3780
agcactctgg acggaagatg gagtgccctg acccccggac ctccaatggc cacggctgga    3840
cctgcggaca gcaagttcag caacagccag ctcatctttg cggggcctaa acagaacggc    3900
aacacggcca ccgtacccgg gactctgatc ttcacctctg aggaggagct ggcagccacc    3960
aacgccacca tacggacat gtggggcaac ctacctggcg tgaccagag caacagcaac    4020 ctgccgaccg tggacagact gacagccttg ggagccgtgc tggaatggt ctggcaaaac    4080 agagacattt actaccaggg tcccatttgg gccaagattc tcataccga tggacacttt    4140 cacccctcac cgctgattgg tgggtttggg ctgaaacacc gcctcctca aattttttatc    4200 aagaacaccc cggtacctgc gaatcctgca acgaccttca gctctactcc ggtaaactcc    4260
ttcattactc agtacagcac tggccaggtg tcggtgcaga ttgactggga gatccagaag    4320
gagcggtcca aacgctggaa ccccgaggtc cagtttacct ccaactacgg acagcaaaac    4380
tctctgttgt gggctcccga tgcggctggg aaatacactg agcctagggc tatcggtacc    4440
cgctacctca cccaccacct gtaataacct gttaatcaat aaaccggttt attcgtttca    4500
gttgaacttt ggtctccgtg tccttcttat cttatctcgt ttccatggct actgcgtaca    4560
taagcagcgg cctgcggcgc ttgcgcttcg cggtttacaa ctgccggtta atcagtaact    4620
tctggcaaac cagatgatgg agttggccac attagctatg cgcgctcgct cactcactcg    4680
gccctggaga ccaaaggtct ccagactgcc ggcctctggc cggcagggcc gagtgagtga    4740
gcgagcgcgc atagagggag tggccaa                                         4767
```

<210> SEQ ID NO 6
<211> LENGTH: 4642
<212> TYPE: DNA
<213> ORGANISM: adeno-associated virus 5

<400> SEQUENCE: 6

```
ctctcccccc tgtcgcgttc gctcgctcgc tggctcgttt ggggggtgg cagctcaaag      60 agctgccaga cgacggccct ctggccgtcg ccccccaaa cgagcagcg agcgagcgaa     120 cgcgacaggg gggagagtgc cacactctca agcaagggg ttttgtaagc agtgatgtca     180
taatgatgta atgcttattg tcacgcgata gttaatgatt aacagtcatg tgatgtgttt     240
tatccaatag gaagaaagcg cgcgtatgag ttctcgcgag acttccgggg tataaaagac     300
cgagtgaacg agcccgccgc cattctttgc tctggactgc tagaggaccc tcgctgccat     360
ggctaccttc tatgaagtca ttgttcgcgt cccatttgac gtgaggaac atctgcctgg     420 aatttctgac agctttgtgg actgggtaac tggtcaaatt tgggagctgc ctccagagtc     480
```

```
agatttaaat tgactctgg ttgaacagcc tcagttgacg gtggctgata gaattcgccg    540
cgtgttcctg tacgagtgga acaaattttc caagcaggag tccaaattct ttgtgcagtt    600
tgaaaaggga tctgaatatt ttcatctgca cacgcttgtg gagacctccg gcatctcttc    660
catggtcctc ggccgctacg tgagtcagat tcgcgcccag ctggtgaaag tggtcttcca    720
gggaattgaa ccccagatca acgactgggt cgccatcacc aaggtaaaga agggcggagc    780
caataaggtg gtggattctg gtatattcc cgcctacctg ctgccgaagg tccaaccgga    840
gcttcagtgg gcgtggacaa acctggacga gtataaattg ccgccctga atctggagga    900 gcgcaaacgg ctcgtcgcgc agtttctggc agaatcctcg cagcgctcgc aggaggcggc    960
ttcgcagcgt gagttctcgg ctgacccggt catcaaaagc aagacttccc agaaatacat   1020
ggcgctcgtc aactggctcg tggagcacgg catcacttcc gagaagcagt ggatccagga   1080
aaatcaggag agctacctct ccttcaactc caccggcaac tctcggagcc agatcaaggc   1140
cgcgctcgac aacgcgacca aaattatgag tctgacaaaa agcgcggtgg actacctcgt   1200
ggggagctcc gttcccgagg acatttcaaa aaacagaatc tggcaaattt ttgagatgaa   1260
tggctacgac ccggcctacg cgggatccat cctctacggc tggtgtcagc gctccttcaa   1320
caagaggaac accgtctggc tctacggacc cgccacgacc ggcaagacca catcgcgga   1380 ggccatcgcc cacactgtgc cttttacgg ctgcgtgaac tggaccaatg aaaactttcc   1440
ctttaatgac tgtgtggaca aatgctcat ttggtgggag gagggaaaga tgaccaacaa   1500
ggtggttgaa tccgccaagg ccatcctggg gggctcaaag gtgcgggtcg atcagaaatg   1560
taaatcctct gttcaaattg attctacccc tgtcattgta acttccaata caaacatgtg   1620
tgtggtggtg gatgggaatt ccacgacctt gaacaccag cagccgctgg aggaccgcat   1680
gttcaaattt gaactgacta gcggctcccc gccagatttt ggcaagatta ctaagcagga   1740
agtcaaggac tttttttgctt gggcaaaggt caatcaggtg ccggtgactc acgagtttaa   1800
agttcccagg gaattggcgg gaactaaagg ggcggagaaa tctctaaaac gcccactggg   1860
tgacgtcacc aatactagct ataaaagtct ggagaagcgg gccaggctct catttgttcc   1920
cgagacgcct cgcagttcag acgtgactgt tgatcccgct cctctgcgac cgctcaattg   1980
gaattcaagg tatgattgca aatgtgacta tcatgctcaa tttgacaaca tttctaacaa   2040
atgtgatgaa tgtgaatatt tgaatcgggg caaaaatgga tgtatctgtc acaatgtaac   2100
tcactgtcaa atttgtcatg ggattccccc ctgggaaaag gaaaacttgt cagattttgg   2160
ggattttgac gatgccaata aagaacagta aataaagcga gtagtcatgt cttttgttga   2220
tcaccctcca gattggttgg aagaagttgg tgaaggtctt cgcgagtttt tgggccttga   2280
agcgggccca ccgaaaccaa acccaatca gcagcatcaa gatcaagccc gtggtcttgt   2340
gctgcctggt tataactatc tcggacccgg aaacggtctc gatcgaggag agcctgtcaa   2400
cagggcagac gaggtcgcgc gagagcacga catctcgtac aacgagcagc ttgaggcggg   2460
agacaacccc tacctcaagt acaaccacgc ggacgccgag tttcaggaga agctcgccga   2520
cgacacatcc ttcgggggaa acctcggaaa ggcagtcttt caggccaaga aaagggttct   2580
cgaacctttt ggcctggttg aagagggtgc taagacggcc cctaccggaa agcggataga   2640
cgaccacttt ccaaaaagaa agaaggctcg gaccgaagag gactccaagc cttccacctc   2700
gtcagacgcc gaagctggac ccagcggatc ccagcagctg caaatcccag cccaaccagc   2760
ctcaagtttg ggagctgata caatgtctgc gggaggtggc ggcccattgg gcgacaataa   2820
```

```
ccaaggtgcc gatggagtgg gcaatgcctc gggagattgg cattgcgatt ccacgtggat    2880
gggggacaga gtcgtcacca agtccacccg aacctgggtg ctgcccagct acaacaacca    2940
ccagtaccga gagatcaaaa gcggctccgt cgacggaagc aacgccaacg cctactttgg    3000
atacagcacc ccctgggggt actttgactt taaccgcttc cacagccact ggagcccccg    3060
agactggcaa agactcatca caactactg gggcttcaga ccccggtccc tcagagtcaa      3120
aatcttcaac attcaagtca aagaggtcac ggtgcaggac tccaccacca ccatcgccaa    3180
caacctcacc tccaccgtcc aagtgtttac ggacgacgac taccagctgc cctacgtcgt    3240
cggcaacggg accgagggat gcctgccggc cttccctccg caggtctta cgctgccgca     3300
gtacggttac gcgacgctga accgcgacaa cacagaaaat cccaccgaga ggagcagctt    3360
cttctgccta gagtactttc ccagcaagat gctgagaacg ggcaacaact ttgagtttac    3420
ctacaacttt gaggaggtgc ccttccactc cagcttcgct cccagtcaga acctgttcaa    3480
gctggccaac ccgctggtgg accagtactt gtaccgcttc gtgagcacaa ataacactgg    3540
cggagtccag ttcaacaaga acctggccgg agatacgcc aacacctaca aaaactggtt     3600
cccgggccc atgggccgaa cccagggctg gaacctgggc tccggggtca accgcgccag      3660
tgtcagcgcc ttcgccacga ccaataggat ggagctcgag ggcgcgagtt accaggtgcc    3720
cccgcagccg aacggcatga ccaacaacct ccagggcagc aacacctatg ccctggagaa    3780
cactatgatc ttcaacagcc agccggcgaa ccccgggcacc accgccacgt acctcgaggg   3840
caacatgctc atcaccagcg agagcgagac gcagccggtg aaccgcgtgg cgtacaacgt    3900
cggcgggcag atgccaccca acaaccagag ctccaccact gccccgcgca ccggcacgta    3960
caacctccag gaaatcgtgc ccggcagcgt gtggatggag agggacgtgt acctccaagg    4020
acccatctgg gccaagatcc cagagacggg ggcgcacttt caccccctctc cggccatggg   4080
cggattcgga ctcaaacacc caccgcccat gatgctcatc aagaacacgc ctgtgcccgg    4140
aaatatcacc agcttctcgg acgtgcccgt cagcagcttc atcacccagt acagcaccgg    4200
gcaggtcacc gtgagatgg agtgggagct caagaaggaa aactccaaga ggtggaaccc     4260
agagatccag tacacaaaca actacaacga cccccagttt gtggactttg ccccggacag    4320
caccggggaa tacagaacca ccagacctat cggaacccga taccttaccc gacccccttta  4380
acccattcat gtcgcatacc ctcaataaac cgtgtattcg tgtcagtaaa atactgcctc    4440
ttgtggtcat tcaatgaata acagcttaca acatctacaa aacctccttg cttgagagtg    4500
tggcactctc ccccctgtcg cgttcgctcg ctcgctggct cgtttggggg ggtggcagct    4560
caaagagctg ccagacgacg gccctctggc cgtcgccccc ccaaacgagc cagcgagcga    4620
gcgaacgcga caggggggag ag                                              4642
```

<210> SEQ ID NO 7
<211> LENGTH: 28
<212> TYPE: DNA
<213> ORGANISM: Artificial Sequence
<220> FEATURE:
<223> OTHER INFORMATION: Primer Sequence

<400> SEQUENCE: 7
ataagcttac gctcagtgga avgaaaac                                         28

<210> SEQ ID NO 8
<211> LENGTH: 34
<212> TYPE: DNA
<213> ORGANISM: Artificial Sequence

```
<220> FEATURE:
<223> OTHER INFORMATION: Primer Sequence

<400> SEQUENCE: 8
ataagcttga cgtgtcagtg tcagtcctgc tcct                              34

<210> SEQ ID NO 9
<211> LENGTH: 19
<212> TYPE: DNA
<213> ORGANISM: Artificial Sequence
<220> FEATURE:
<223> OTHER INFORMATION: Primer Sequence

<400> SEQUENCE: 9
taacaacata ggagctgtg                                               19

<210> SEQ ID NO 10
<211> LENGTH: 20
<212> TYPE: DNA
<213> ORGANISM: Artificial Sequence
<220> FEATURE:
<223> OTHER INFORMATION: Primer Sequence

<400> SEQUENCE: 10
cagatacgcg tttcctagga                                              20

<210> SEQ ID NO 11
<211> LENGTH: 11
<212> TYPE: DNA
<213> ORGANISM: Artificial Sequence
<220> FEATURE:
<223> OTHER INFORMATION: Sm domain

<400> SEQUENCE: 11
aatttgtcta g                                                       11

<210> SEQ ID NO 12
<211> LENGTH: 11
<212> TYPE: DNA
<213> ORGANISM: Artificial Sequence
<220> FEATURE:
<223> OTHER INFORMATION: smOPT

<400> SEQUENCE: 12
aatttttgga g                                                       11

<210> SEQ ID NO 13
<211> LENGTH: 24
<212> TYPE: DNA
<213> ORGANISM: Mus musculus

<400> SEQUENCE: 13
aaatagaagt tcatttacac taac                                         24

<210> SEQ ID NO 14
<211> LENGTH: 20
<212> TYPE: DNA
<213> ORGANISM: Mus musculus

<400> SEQUENCE: 14
ggccaaacct cggcttacct                                              20
```